United States Patent [19]

Yerlikaya et al.

[11] Patent Number: 5,415,641
[45] Date of Patent: May 16, 1995

[54] DROP DETECTION METHOD AND APPARATUS

[75] Inventors: Denis Y. Yerlikaya, Des Peres; Randall J. Krohn, Ballwin, both of Mo.

[73] Assignee: Sherwood Medical Company, St. Louis, Mo.

[21] Appl. No.: 970,323

[22] Filed: Nov. 2, 1992

Related U.S. Application Data

[63] Continuation-in-part of Ser. No. 861,672, Apr. 1, 1992, Pat. No. 5,346,466, which is a continuation-in-part of Ser. No. 678,639, Apr. 1, 1991, Pat. No. 5,256,155.

[51] Int. Cl.$^6$ .............................................. A61M 5/00
[52] U.S. Cl. .................................................... 604/251
[58] Field of Search ................... 604/250, 253, 65–67, 604/246, 251, 255, 30–31; 128/DIG. 12–DIG. 13

[56] References Cited

U.S. PATENT DOCUMENTS

| | | | |
|---|---|---|---|
| 4,085,699 | 11/1977 | Van Vloten | 219/121 LM |
| 4,490,140 | 12/1984 | Carr et al. | 604/65 |
| 4,498,901 | 2/1985 | Finch | 604/253 |
| 4,533,350 | 8/1965 | Danby et al. | 604/253 |
| 4,680,462 | 7/1987 | Kamen | 250/222.1 |
| 4,718,896 | 1/1988 | Arndt et al. | 604/253 |
| 4,720,636 | 1/1988 | Benner, Jr. | 250/573 |
| 4,786,800 | 11/1988 | Kamen | 250/222.1 |
| 5,012,496 | 4/1991 | Weinreb et al. | 377/21 |
| 5,045,069 | 9/1991 | Imparato | 604/251 |

FOREIGN PATENT DOCUMENTS 0209659 1/1987 European Pat. Off. .
8603002 5/1986 WIPO .

Primary Examiner—John D. Yasko
Assistant Examiner—Manuel A. Mendez
Attorney, Agent, or Firm—Montgomery W. Smith; Curtis D. Kinghorn; Gene B. Kartchner

[57] ABSTRACT

A drop detector circuit and method are provided for a drop detector of the type including a drop chamber and a light emitter and corresponding detector located on opposite sides of the drop chamber. The detector is saturated by light emitted from the light emitter to produce a saturated detector output signal. The detector circuit senses variations in the detector output signal caused by drops passing through the drop chamber between the emitter and detector that block light emitted by the emitter from reaching the detector. The detector circuit senses the slope of the variations in the detector output signal and produces a control signal when the slope exceeds a threshold value.

25 Claims, 29 Drawing Sheets

DROP DETECTION METHOD AND APPARATUS

This application is a continuation-in-part of application Ser. No. 07/861,672, filed on Apr. 1, 1992, and now U.S. Pat. No. 5,346,466 which is a continuation-in-part of application Ser. No. 07/678,639, filed on Apr. 1, 1991, and now U.S. Pat. No. 5,256,155.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

The invention relates generally to drop detection in a medical liquid drop chamber and, more specifically, concerns a drop detection method and apparatus for use in an ambulatory or household environment.

2. Description of Related Art

Medical drop chambers are used in various medical devices for metering and monitoring the flow rate of a fluid being administered to a patient. In a given drop chamber, each drop has a uniform volume of fluid. Therefore, by counting the number of drops falling in a given time period, the flow rate can be calculated easily. Such drop chambers are used, for example, in gravity-driven or pump-driven infusion systems.

Devices are known in the art for automatically sensing the drops in a chamber. These may, for example, be connected to circuits that can compute and display the flow rate or to alarms that indicate when the flow rate is too high or too low. These drop detectors are often optical sensors that react to a drop breaking optical communication between a light source and a sensor. In a controlled environment, such as a hospital, few outside conditions affect the optical sensors. The ambient light is fairly uniform throughout the environment and the drop chamber is relatively immobile and usually kept upright.

However, in either an ambulatory or household environment, several factors that may affect the optical sensors must be handled properly by the drop sensor to avoid false readings or alarms. These factors include widely varying ambient light conditions and excessive movement and tilting of the drop chamber, especially in ambulatory situations. False readings caused by these factors are a major reason for physicians' reluctance to use the ambulatory devices. It has therefore been a goal in the art that the drop detectors be capable of increased sensitivity to the drops, while being immune to the ambient light variation or movement and change in orientation of the chamber.

U.S. Pat. No. 4,720,636 to Benner, Jr. discloses a drop detection structure and detection circuitry that includes two photodetectors, one for sensing a decrease in light caused by a drop passing in front of it, and another for detecting an increase in light caused when a drop passes nearby and reflects additional light. A drop would pass nearby, for example, if the chamber were tilted. However, in the event of a very high tilt angle, coherent drops are not always formed. The liquid may enter the chamber and immediately spread onto the interior surface of the chamber, rather than falling to the bottom of the chamber.

U.S. Pat. No. 4,718,896 to Arndt et al. discloses a drop detector that includes an array of light emitter/sensor pairs arranged to detect drops falling at angles of up to 30 degrees from the normal, vertical orientation. Tilt angles greater than 30 degrees are found in everyday use of the medical devices containing these detectors, rendering the detectors of this patent only partially effective.

SUMMARY OF THE INVENTION

A drop detector system and circuit is provided. The system includes an infrared light emitter and detector system for detecting drops passing between the emitter and detector. When no drop is passing between the emitter;and detector, the detector is saturated by light emitted from the emitter. The resulting detector output signal is at a constant relatively high level. The drops passing between the emitter and detector block a portion of the light emitted from the emitter and thereby prevents the blocked portion of light from impinging on the detector. The drop detector circuit senses the passing of a drop between the emitter and detector by sensing the drop in the detector output signal when the passing drop blocks some of the light impinging on the detector. Saturating the detector and detecting the drop in voltage in the detector output signal ameliorates the system's ability to detect passing drops despite the effect of changing ambient light on the circuit.

The detector output signal is amplified, passed through a low pass filter and passed through a differentiator circuit-to further block signals caused by artifacts including ambient light and residual filtering effects. The drop detector circuit senses a drop passing between the emitter and detector by sensing a drop in the voltage of the detector, output signal having a slope above a certain threshold. This allows the system to detect more than one drop passing between the emitter and detector, at a time. This also allows the system to detect an occluded feeding tube by sensing fewer than the expected drops within the pump's operating cycle.

It is thus an object of the invention to provide an improved drop detector for a liquid drop chamber which is capable of detecting drops in a variety of conditions and applications, including tilting of the device and relatively intense or varying ambient light, without causing false readouts or alarms.

It is a further object of the invention to provide an improved drop detector that is immune to changes in ambient light.

It is a further object of the invention to provide an improved drop detector that can detect drops at tilt angles of up to 80 degrees from the normal, vertical positioning of the drop chamber.

It is a further object of the invention to be able to generate and display an error message when an insufficient number of drops pass through the drop sensor while pumping.

It is a still further object of the invention that the improved drop detector be constructed of readily available components and be cost-efficient and relatively inexpensive to manufacture.

It is still another object of the invention to detect the occlusion of the feeding tube so that appropriate action can be taken.

The foregoing and other objects and advantages of this invention will be appreciated more fully upon reading the following detailed description of a preferred embodiment in conjunction with the appended drawings.

BRIEF DESCRIPTION OF THE DRAWINGS

The preferred embodiments of the invention are described herein with reference to the appended drawings, wherein.

DETAILED DESCRIPTION OF THE PREFERRED EMBODIMENTS

Figure 1:
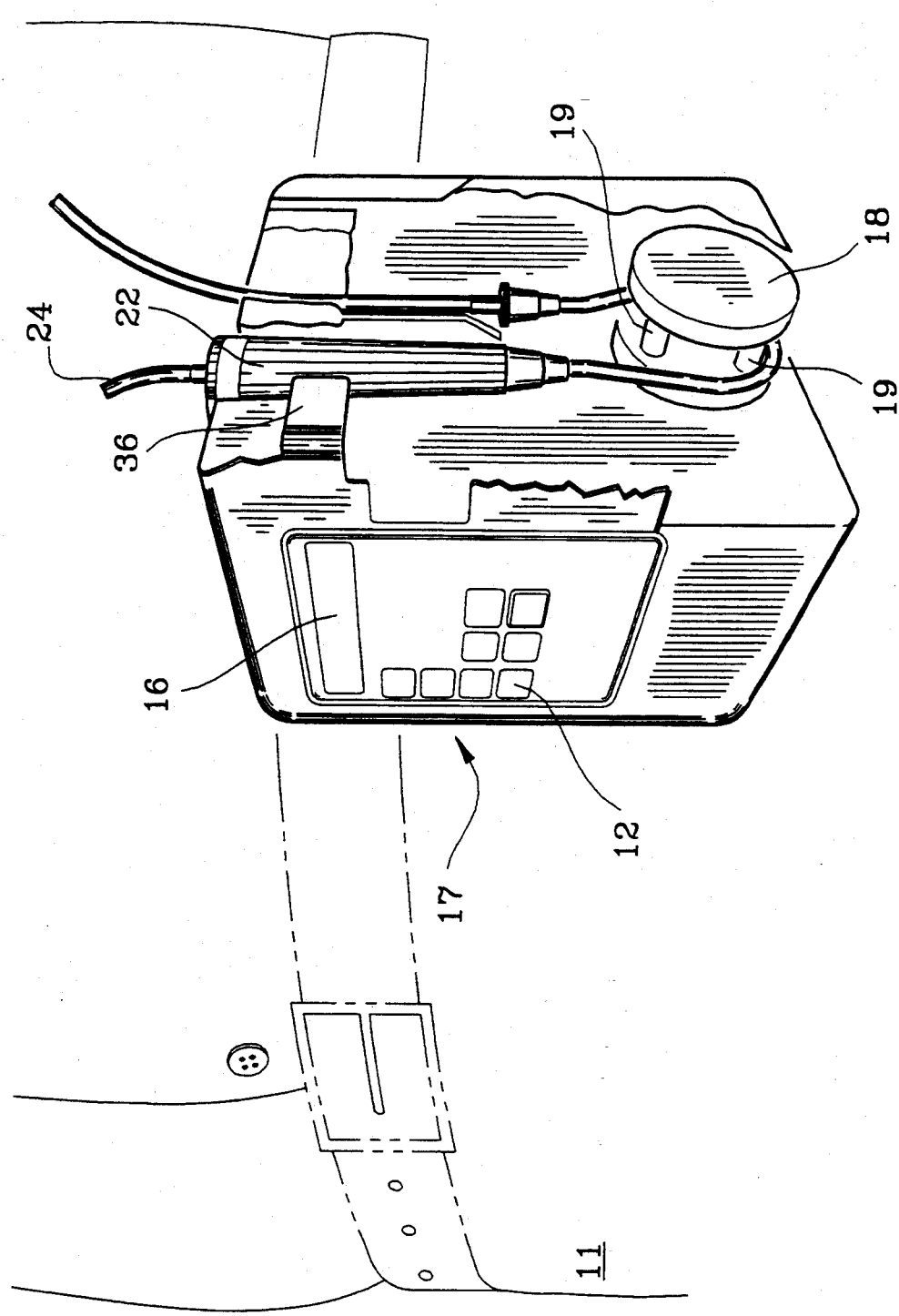
FIG. 1 is a perspective view illustrating the manner in which an ambulatory patient could use a drop detection apparatus embodying the invention.

In FIG. 1, a medical infusion device worn by a patient is generally designated by the reference numeral 10. The infusion device includes a pump for the enteral administration of fluids. It is to be understood that while the preferred embodiment is shown for a medical infusion device, the invention can be similarly used with any device making use of a drop chamber.

As can be seen in FIG. 1, the device is capable of being attached to the belt of a patient 11 in use, while the patient 11 is completely ambulatory. The device is thus subjected to significant tilting, jarring, and accelerations that must be accurately compensated for in the internal mechanisms and circuits of the device 10.

Figure 2:
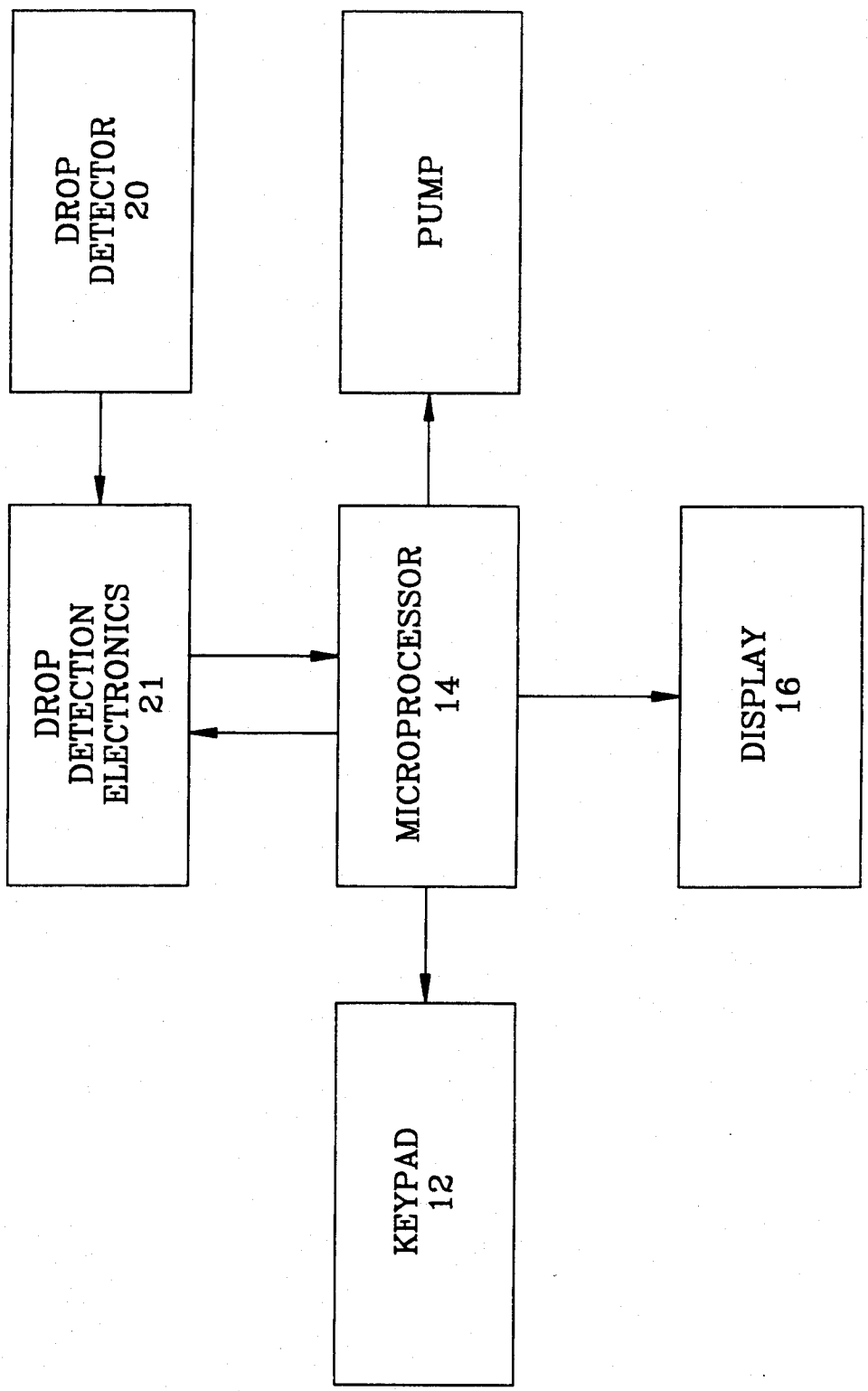
FIG. 2 is a functional block diagram of a drop detection apparatus embodying the invention.

The block diagram of FIG. 2 represents the electrical interaction of the major electronic and electromechanical components of the device 16 and shows signal connections. A keypad 12 allows operator input of device parameters, such as fluid flow rate, which are sent to a microprocessor 14. The microprocessor 14, in turn, provides information to the patient on a display 16 and controls a motor-driven pump 17. Drop detector 20, described in detail below, has a drop chamber which is interposed in the fluid flow path between a fluid supply (not shown) and the pump 17. A sensor monitoring the drop chamber detects the flow of fluid through the drop chamber and sends corresponding signals to drop detection electronics 21. The electronics 21 filters unwanted components in the signals from the detector 20 and passes the remainder to the microprocessor 14. The microprocessor 14 also returns control signals to the electronics 21, as described below.

In operation, the pump 17 feeds fluid for the patient at a rate set into the device by means of the keypad 12 and maintained by the microprocessor 14. All of the fluid that the pump 17 feeds to the patient 11 must pass through a drop chamber 22 and no dripping occurs if the pump stops feeding fluid. Drop detection confirms to the microprocessor 14 that the pump 17 is operating correctly. Accurate drop detection therefore permits accurate control of the pump by the microprocessor 14.

Figure 5:
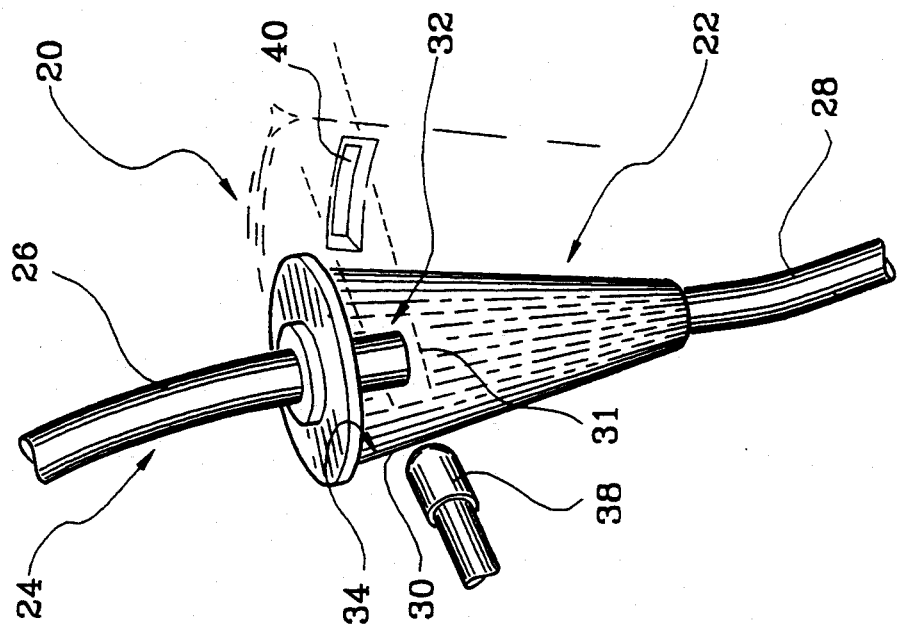
FIG. 5 is a perspective view of a drop chamber and drop detector assembly, showing the optical path coverage of the drop detector.

FIG. 5 illustrates the removable drop chamber 22, connected in series with and interrupting a delivery tube 24 that runs from a fluid source (not shown) to a patient (11 in FIG. 1). Fluid enters the drop chamber 22 from the top portion 26 of the tube 24 as shown in FIG. 5 and exits the chamber 22 through the bottom portion 28. The drop chamber 22 is a sealed unit, except for the entrance and exit portions 26,28 of the tube 24, which penetrate the top and bottom of the chamber 22, respectively. The chamber 22 has a generally frusto-conical light-transmissive sidewall 30, with the smaller diameter at its bottom. The top portion 26 of the tube 24 extends partially into the chamber 22, creating a drop formation area 32. Fluid accumulates at this area 32, until it forms a complete drop, which then falls to the bottom portion 28 of drop chamber 22.

When the drop chamber 22 is tilted, as often happens when the infusion device is used in an ambulatory manner shown in FIG. 1, the drops will not fall to the bottom portion 28 of drop chamber 22, but will fall onto the side of the sloped sidewall 30 of drop chamber 22. The tilt angle determines where the drop will hit the sidewall 30. At tilt angles above 70 degrees from vertical, the drops do not even fall, but tend to form a puddle on the sidewall 30 at position 34 and then slide down sidewall 30.

Figure 4:
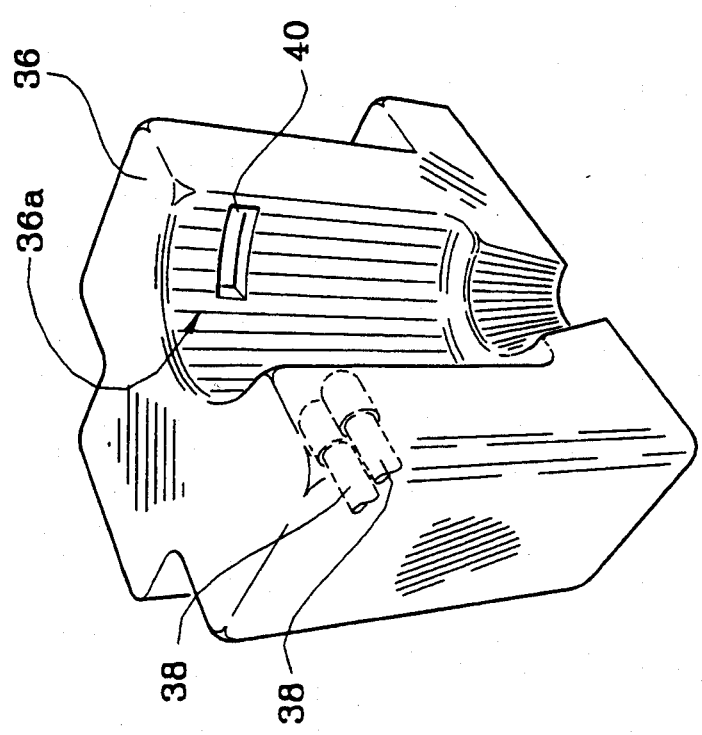
FIG. 4 is a perspective view of a portion of the infusion device, showing a mounting receptacle for a drop detector assembly.
Figure 6:
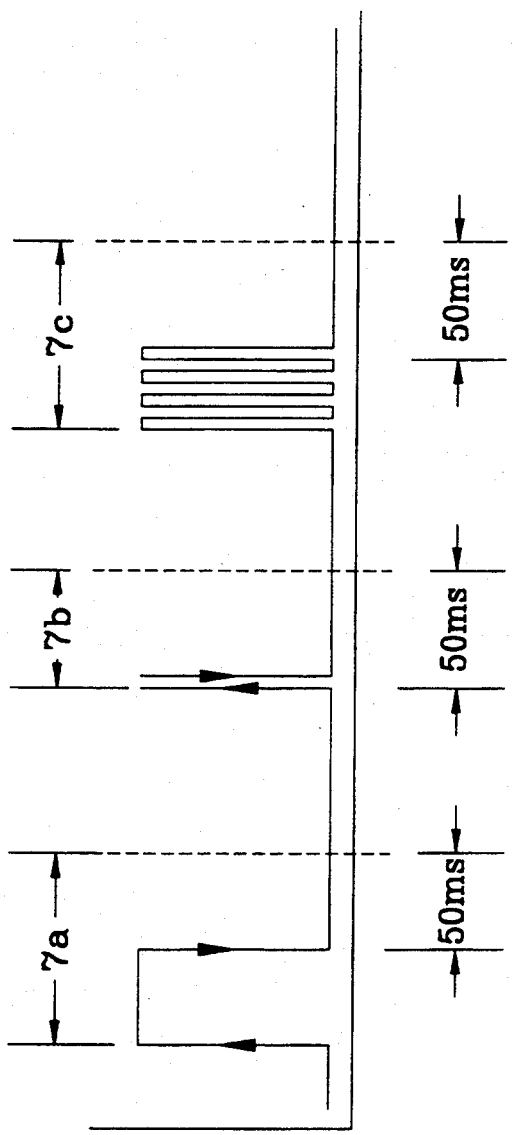
FIG. 6 illustrates typical output waveforms of the drop detection circuit as in FIG. 3.
Figure 7:
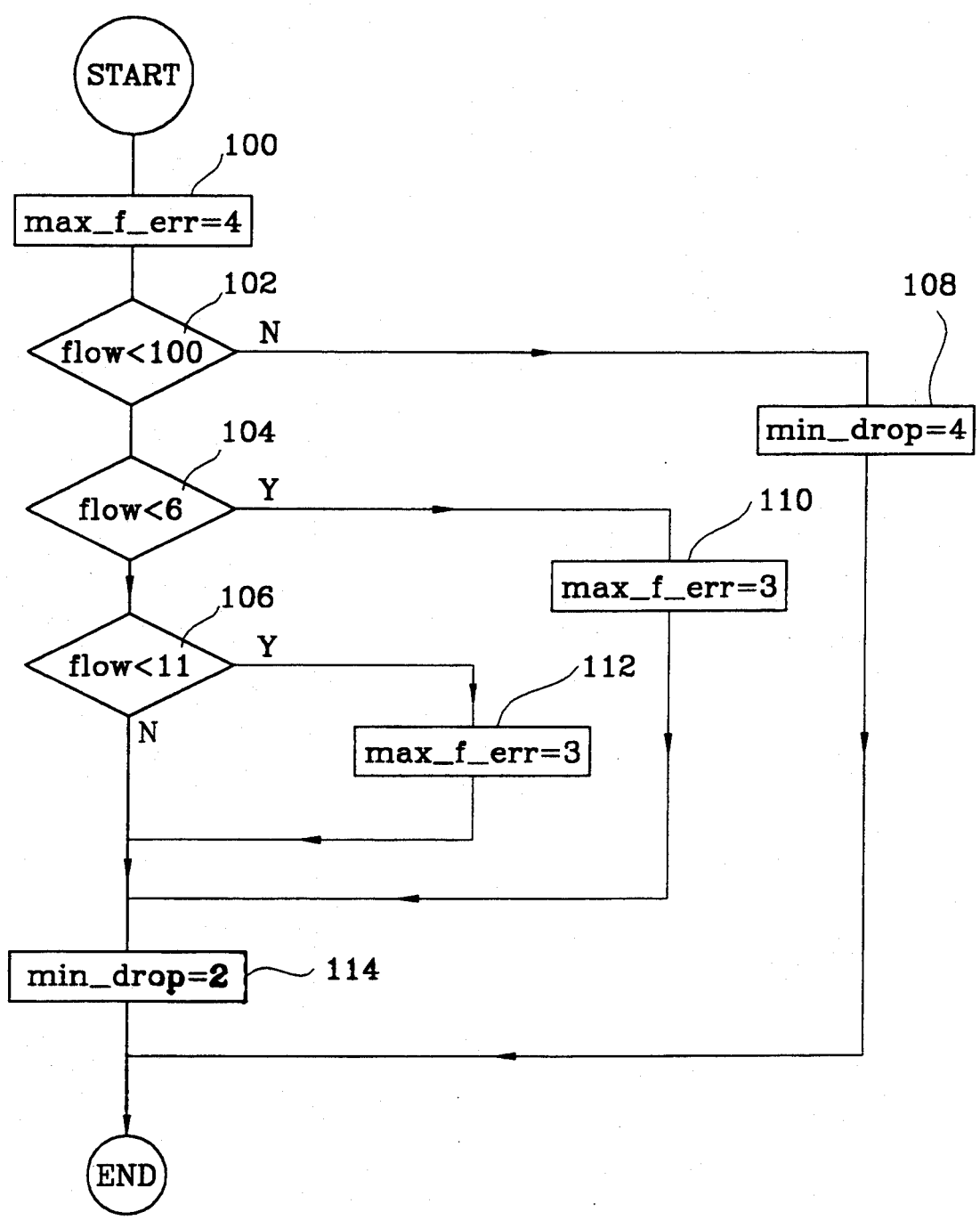
FIG. 7 is a flow chart representing the drop discrimination process utilized in an apparatus embodying the invention.

Drop detector 20 includes a yoke 36 (see FIG. 4), which is mounted on device 10 and a drop chamber 22 (see FIG. 5), which is removably received within yoke 36, thus supporting the drop chamber 22 in the infusion device 10. Yoke 36 has a passageway 36a, which receives drop chamber 22 in an upright position.

The drop detection system described herein depends on drops of the fluid to be pumped being formed at the drop formation area 32. Although there are many ways to pump the fluid to the drop chamber 22, the preferred embodiment of the pump 17 is a peristaltic pump. In the peristaltic pump 17, a tube 24 connects a fluid source (not shown) to the patient 11 (FIG. 1) through drop chamber 22. A portion of tube 24 is wrapped around a motorized rotor 18 having a series of rollers 19 on its outer surface. The rotation of the rotor 18 is controlled by microprocessor 14. When the rotor 18 turns, the rollers 19 roll across tube 24 wrapped around rotor 18 thereby pushing the fluid within the tube 24 to the drop formation area 32. At the drop formation area 32, drops are formed and the fluid is forced into the drop chamber 22 as drops that fall or slide along the wall of the drop chamber 22 to the drop chamber bottom portion 28.

Experience has shown that for a given fluid, a relatively constant number of drops are formed at drop formation area 32 per each passing of a roller 19 along tube 24. In the preferred embodiment of the pump 17, there are three rollers 19 on the rotor 18 so that a complete revolution of rotor 18 causes the three rollers 19 to contact tube 24 and force fluid to the drop formation area 32.

In FIGS. 17 through 32, the trace labeled G is "high" when rotor 18 is rotating and "low" when rotor 18 is not rotating. A "cycle" is defined as the start of rotation of rotor 18 ("H" in FIGS. 17–32) to the next start of rotation of rotor 18 ("H'" in FIGS. 17–32). In the preferred embodiment of the invention, at flow rates less than 100 ml/hour, the rotor 18 will rotate for ⅓ revolution, so that one roller 19 rolls over the tube 24, and then pause before the next ⅓ rotation of the rotor 18. In this case, there are three "cycles" per complete revolution of the rotor 18.

At flow rates of 100 ml/hour and above, rotor 18 turns for a complete revolution before pausing before the start of the next revolution. On each complete rotation of rotor 18, the three rollers 19 contact the tube 24. Drops are formed at drop formation area 32 as each roller 19 rolls over the tube 24. As a result, at these flow rates, there are three sets of drops produced per "cycle".

With the fluids typically used in enteral feeding pumps, at flow rates below 100 ml/hour, a minimum of two drops are formed at the drop formation area 32 per "cycle". At flow rates above 100 ml/hour, a minimum of four drops are formed at drop formation area 32 per "cycle". The actual number of drops formed depends on the viscosity of the fluid; the more viscous fluids produce the minimum number of drops while the less viscous fluids like water produce higher than the minimum number of drops per "cycle".

In the preferred embodiment of the peristaltic pump 17, the speed of rotation of the rotor 18 is a constant. The rate of fluid movement through the pump 17 is controlled by causing the rotor 18 to rotate through ⅓ or a full revolution, depending on the flow rate, and then stop rotating for a wait time ("J" in FIGS. 17–32) before rotating through the next ⅓ or full revolution, respectively. Because the speed of rotation of the rotor 18 is constant, the amount of time ("K" in FIGS. 17–32) required for the rotor 18 to rotate through the ⅓ or full revolution is constant for all flow rates below 95 ml/hour and above 100 ml/hour respectively. Consequently, the amount of time K that rotor 18 is rotating, at a designated flow rate, to cause the drops to be produced is a constant.

However, the wait time J the rotor 18 pauses without moving after the completion of the ⅓ or full revolution and before the beginning of the next ⅓ or full revolution varies. As a result, the number of drops passing through the drop chamber 22 per the time the pump 17 takes to complete a "cycle" (J+K), which is proportional to the flow rate, may vary widely. This allows pump 17 to provide a large spectrum of flow rates.

For example, if the rotational speed of the rotor is 30 revolutions per minute (R.P.M.), a complete rotation of rotor 18 will take two seconds. The time required to complete ⅓ revolution is then ⅔ second. The wait time J after the end of the rotation of rotor 18 and before the beginning of the next rotation of rotor 18 varies from as short as virtually no time to as long as many minutes. Of course the flow rate where there is a short wait time J between the end of one rotation of rotor 18 and the beginning of the next rotation is the highest flow rate while the flow rates where there are longer wait times J between the end of one rotation of rotor 18 and the beginning of the next produces the lowest flow rates.

When the pump 17 is operating properly, the following minimum number of drops per "cycle" are expected to detected:

| Flow rate in ml/hr | Drops/"cycle" |
| --- | --- |
| 1–95 | 2 drops |
| 100–400 | 4 drops |

In the preferred embodiment of the device 10, flow rates above 95 ml/hour may only be set in increments of 5 ml/hour.

Although a peristaltic pump is the preferred embodiment for pump 17, other pumps having drop chambers may use the invention. Further, although the invention described herein is described as incorporated with a peristaltic pump, the invention may be incorporated with any other type pump as will be clear to those skilled in the art.

Figure 11:
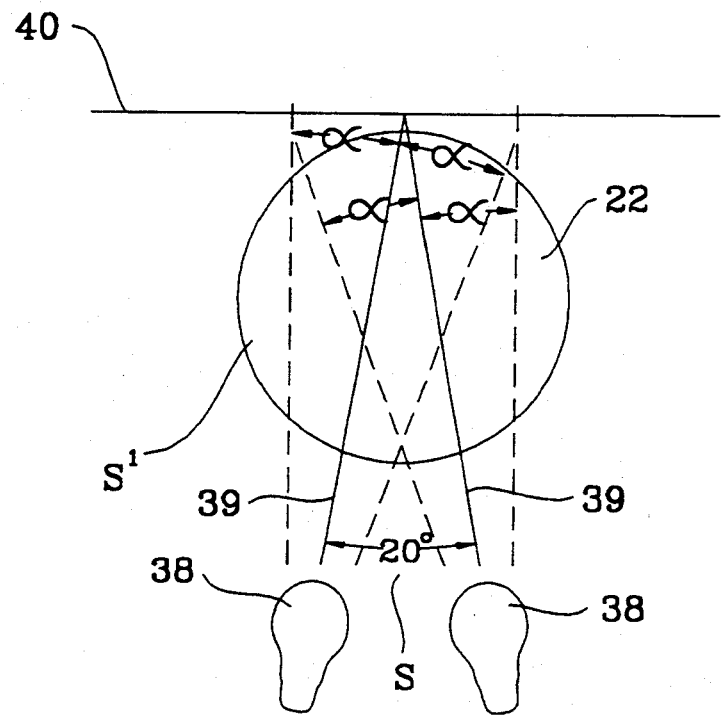
FIG. 11 is a cross-sectional view of one embodiment of the invention.

In a first preferred embodiment shown in FIG. 11, two light sources 38, which are preferably infrared light emitting diodes, preferably Seimens SFH 485-2 IRLEDs, are mounted side-by-side, so as to face into passageway 36a and drop chamber 22. As shown in FIG. 11, diodes 38 have a 50% illumination angle e which in the case of the Seimens SFH 485-2 IRLEDs is about 16 degrees on either side of the main axis of illumination 39. Again as shown in FIG. 11, diodes 38 are preferably directed toward each other so that the main axes of illumination 39 form an angle of 20 degrees. Diodes 38 are positioned in yoke 36 apart from each other opposite a detector 40 so that the main axes of illumination 39 intersect near detector 40 as will be described in detail hereafter. As shown in FIG. 11, this positioning of diodes 38 combined with the width of illumination by diodes 38 represented by the angle $\alpha$ illuminates virtually the entire cross-section of the drop chamber 22. This arrangement also provides for an overlap of illumination by diodes 38 in the center area of drop chamber 22, the area most likely to have a drop falling through it when the device 10 is not tilted significantly. The significance of this overlapping illumination pattern will be described hereafter in connection with the description of the detectors 40.

In an alternate embodiment, the main axes of illumination 39 may be positioned to intersect at the central axis of drop chamber 22. This alignment creates more of an overlap of the beams of diodes 38 than in the alignment described above but produces a smaller cross-sectional area of illumination within drop chamber 22 than the just described alignment due to the increased overlap of the beams.

Figure 12:
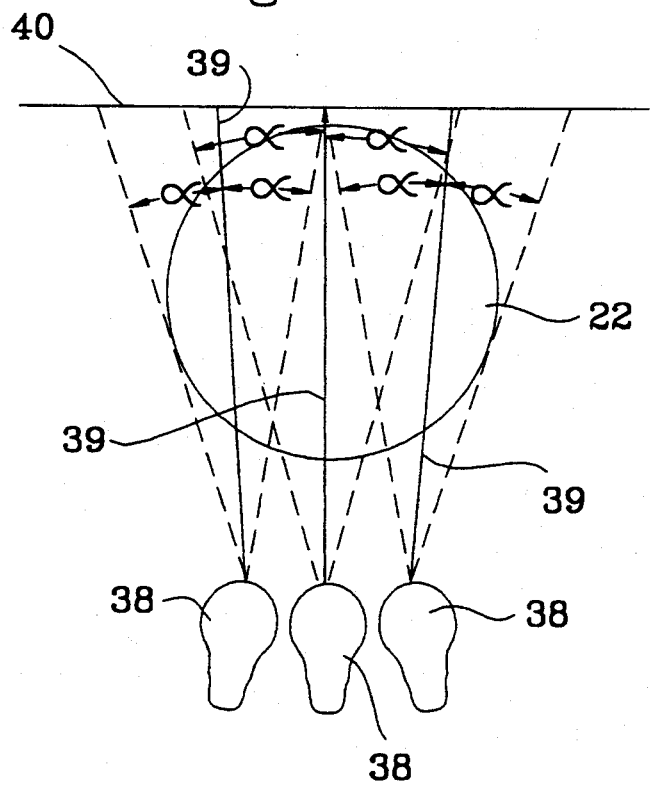
FIG. 12 is a cross-sectional view of another embodiment of the invention.

In a further alternate embodiment, instead of using two diodes 38, three or more diodes could be placed around yoke 36 to illuminate drop chamber 22. In particular, as shown in FIG. 12, three diodes 38 could be arranged so that the main axis of illumination 39 of the middle diode is directed along the diameter of the drop detector chamber 22 from one side of yoke 36 to the other. Two additional diodes 38 are located on either side of the center diode 38 so that each of their most center directed lines of 50% illumination intersect the main axis of illumination 39 of the center diode 38 at detector 40. In this way, virtually the entire cross-sectional area of drop detection chamber 22 is illuminated more particularly the outer fringes of the drop chamber 22 are more brightly illuminated.

Mounted within the yoke 36 on the opposite side of the drop chamber 22 from the IRLEDs 38 is a detector 40. In the preferred embodiment, detector 40 is a rectangular photodiode, preferably a Vactec VTS 3092 photodiode, measuring 0.6 by 0.1 inches (1.52 by 0.25 cm). It is mounted with its length parallel to the horizontal plane. The result of having two IRLEDs 38 opposite a single photodiode 40 is to create a triangular optical path 41, as viewed from above, that can be broken by a drop passing through any portion of the horizontal cross section of drop chamber 22 (as shown in FIG. 5). If a drop contacts the sidewall 30 of drop chamber 22 and then slides down the wall 30, regardless of which side it travels on, the drop will pass through the optical path between the two IRLEDs 38 and the photodiode 40. Because the yoke 36 that holds the drop chamber 22 and the photodiode 40 is not completely sealed (as the drop chamber 22 and tube 24 are removable), ambient light is constantly detected by the photodiode 40, as well as light from the IRLEDs 38. This will be discussed in greater detail below.

Detector 40 is a photovoltaic device that produces an electrical current when light impinges on it. The strength of the current is proportional to the amount of light impinging on detector 40. The current is grounded through a resistor to produce a voltage, called the detector output signal, that is passed to the drop detection circuit 21 for processing as will be described in detail later.

Figure 33:
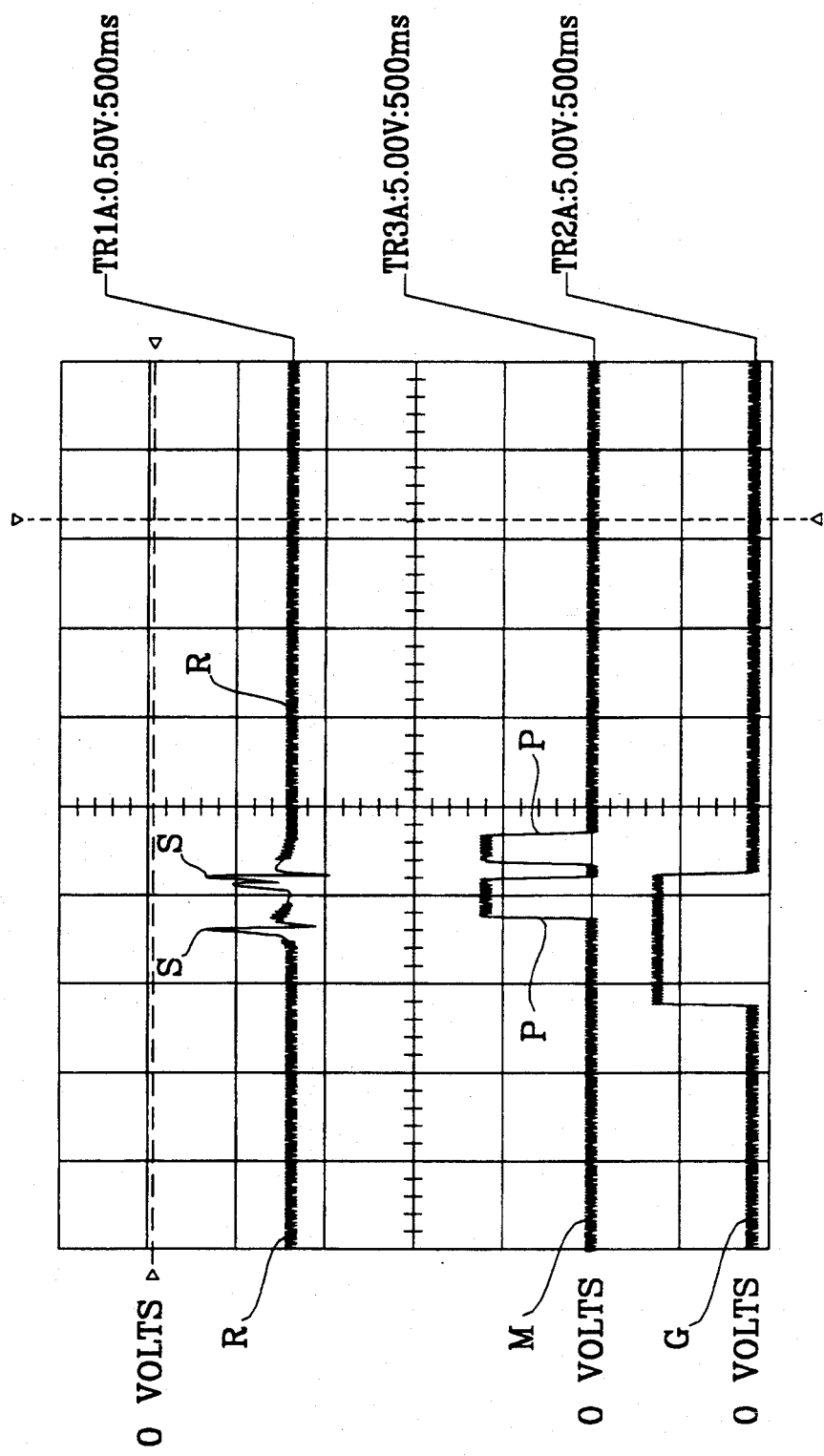
FIG. 33 is a trace of the detector output signal, the output of the invention at point M when the invention is pumping water at a flow rate of 95 ml/hour and at a 0° tilt relative to the central axis of the drop chamber and a trace of the motor control signal.

In the preferred embodiment, the anode side of the diode is tied to negative voltage and the resistor is grounded. Therefore, the voltage level of the detector output signal when light from IRLEDs 38 impinges on detector 40 is a relatively constant negative signal labeled "R" in FIG. 33. Further, any variations in the detector output signal resulting from a drop passing through drop chamber 22 and blocking light emitted from IRLEDs 38 will manifest itself as a positive going signal ("S" in FIG. 33) from the relatively constant negative signal.

In an alternate embodiment, a single detector 40 may be replaced by a series of two or more detectors located circumferentially on yoke 36 on the opposite side of drop chamber 22 from diodes 38.

In another alternate embodiment, the rectangular photodiode detector 40 may be replaced by an infrared sensitive film such as fluorocarbon PVDF, such as that manufactured under the trademark KYNAR.

In a further alternative embodiment, instead of aligning multiple detectors 40 or a fluorocarbon PVDF film detector 40 in a plane on the opposite side of drop detection chamber 22 from diodes 38, detector(s) 40 may be located in yoke 36 on a curve around drop detection chamber 22. One preferred curve is where detector(s) 40 are located an equal distance from the outer edge of drop detection chamber 22. In a variation on this embodiment, diodes 38 and detectors 40 may be interspersed on yoke 36 around the outer surface of drop detection chamber 22.

In all the embodiments of various numbers and arrangements of diodes 38 and detectors 40, the objective is to illuminate the largest percentage of drop detection chamber 22 and to produce the most detectable signal at detector 40 resulting from the blockage of light emitted by diode 38 by the drop either falling through or moving along the edge of drop detection chamber 22.

Because light from diodes 38 spreads out by the angle $\alpha$ from the main axes of illumination 39, there is a space S between diodes 38 and spaces S' outside of the angle $\alpha$ of 50% intensity where only light emitted from diodes 38 having an intensity less than 50% of the maximum illumination value will be present. Diodes 38 should be located around yoke 36 so that the area of spaces S and S' within the drop detection chamber 22 are minimized. This may be accomplished by moving diodes 38 away from the outer edge of drop detection chamber 22.

Also, although the illumination in spaces S and S' are less than 50% of the maximum illumination, there is still illumination in this area. If a drop falls near or within space S it may still be detected by detector 40 because the drop is relatively near to diode 38 thereby causing a relatively large shadow on detector 40 compared to a drop falling closer to detector 40. Further, because the cross-sectional area of the drop occupies a large percentage of the cross-sectional area of the drop detection chamber 22, a drop falling near the diodes 38, including a drop falling in or near space S, will likely also have a portion of the drop within the 50% of maximum illumination area of illumination. Because of this, the drop will likely block enough light from diode 38 to be detected by detector 40 and its corresponding circuitry.

The objective of detecting a drop falling through a drop detection chamber that may be tilted at an angle from vertical may also be accomplished through another species of the invention as described in the following. These species makes use of the property of ellipses that light emitted at one focal point of an ellipse with a reflective inner surface will be focused at the second focal point.

Figure 13:
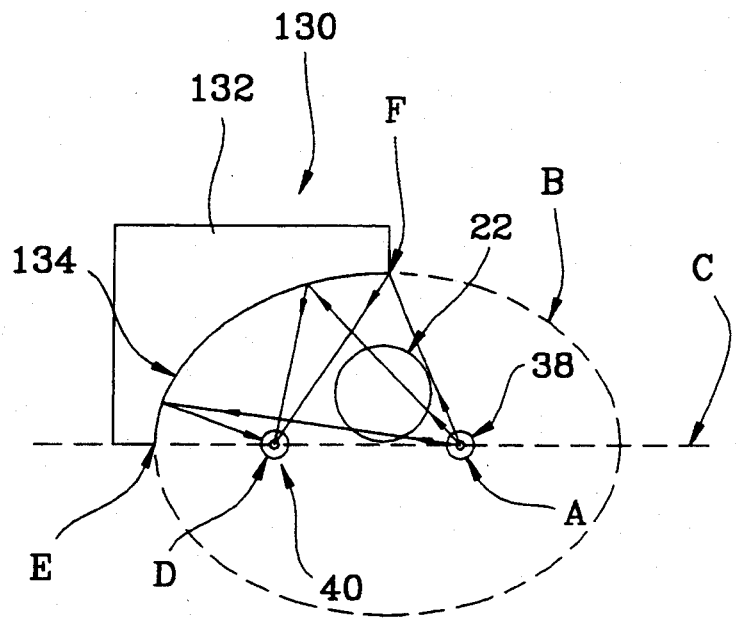
FIG. 13 is a cross-sectional view of another embodiment of the invention.

As shown in FIG. 13, one embodiment of this species of drop detection device uses an elliptical reflector assembly 130 to scan a wide area within the drop chamber 22 for passing drops with the use of a single light source 38 and a single light detector 40. A light source 38 is located at a focal point A of an ellipse B (shown in dotted outline). An elliptical reflector 132 having a reflective surface 134 along the outline of the ellipse B is placed around a portion of the periphery of the ellipse. The reflector 132 preferably includes only a portion of the ellipse, although a reflector 132 encompassing the entire inner surface of the ellipse may be used. In the most preferred embodiment, the inner surface 134 extends from a point E on the surface of ellipse B intersecting a line C drawn through focal points A and D, to a point F on the surface of ellipse B midway between focal points A and D. The exact location of the termination of the reflective surface 134 is not critical so long as most light emitted from light source 38 and passing through drop detector 22 is likely to impinge on reflective surface 134 so that it will be focused at focal point D.

A detector 40 is placed at focal point D. The drop chamber 22 may be placed anywhere within the inside of the ellipse between the light source 38 and the reflective inner surface 134. Experience has shown that if the drop chamber 22 is placed relatively close to the light source 38, the shadow caused by the drops falling through drop chamber 22 will be larger and thus more detectable at detector 40 than if drop chamber 22 is placed relatively further away from the light source 38.

As can be seen with reference to FIG. 13, light emitted from light source 38 will pass through drop detector 22 and then be reflected off the elliptical inner reflective surface 134 which will focus the light at focus D on light detector 40. Even though there will be some refractions and reflections of light on the surface of the drop chamber 22 and also as a result of interaction of light from light source 38 with the falling drops, the majority of the light emitted through the drop chamber 22 will be approximately focused at the light detector 40. As a result, a drop falling through the drop chamber 22 will cause a measurable decrease in light detected by the detector 40.

In an alternate embodiment, a light pipe insert may be used in place of the elliptical reflector 132. Light pipe 136 (FIG. 15) is preferably made of a solid transparent material such as plastic or glass. However, light pipe 136 may be hollow with transparent walls, as will be described hereafter, made of glass, plastic or similar material. In this embodiment, shown in FIG. 14, light pipe 136 has an alternate outer elliptical surface 138. The shape of elliptical surface 138 corresponds to the surface of an ellipse B' having focal points A' and D'.

Light pipe 136 has an inner surface 140 approximately in contact with the drop chamber 22. Ideally, inner surface 140 is curved with a radius of curvature extending from light source 38 and being just long enough to avoid touching drop chamber 22. Inner surface 140 has this curvature so that light from light source 38, in the absence of refraction by drop chamber 22, will strike inner surface at a right angle. Because inner surface 140 is relatively close to drop chamber 22, even light from light source 38 which is refracted by drop chamber 22 will likely strike inner surface 140 at an angle very near a right angle. Because light from light source 38 strikes inner surface 140 at near a right angle, most of this light will enter light pipe 136 and not be reflected at inner surface 140.

Light pipe 136 has an outer surface 142 defined by a line C' extending between the focal points A' and D' and beyond the focal point D'. A further outer surface 144 connects the outer elliptical-surface 138 with the inner surface 140.

The outer elliptical surface 138 is coated with a reflective material so that it forms a reflective surface toward the inside of ellipse B'. The entire surface 142 is preferably coated with a mat surface to minimize stray or unintentional reflections off these surfaces due to the fact that a incomplete ellipse is being used. In addition, because surface 142 has a mat surface, light leaving light source 38 at a very acute angle to line c", when reflected off of surface 138 will not be internally reflected at surface 142, but will instead be diffused into detector 40 as will be described. Surface 144 is also preferably coated with a reflective surface to keep diffracted light within the light pipe 136. Inner surface 140 is transparent so that the light emitted from light source 138 and passing through the drop chamber 22 will pass substantially unimpeded into the light pipe 136.

As before, a light source 38 is placed at a focal point A' of the ellipse B'. A light detector 40 is located on outer surface 142 at focal point D'. Light from light source 38 passes through drop chamber 22 and into light pipe 136. There, the light reflects off of the reflective coating on surface 138 and is focused at focal point D' on detector 40.

A block 146 may be used to position and retain light pipe 136 in position with respect to drop chamber 22 and light source 38.

Although the description of this species is described as containing only one light source 38 and one light detector 40, a cluster of light sources positioned at focal point A,A' or a cluster of light detectors positioned at focal point D,D', together or in combination with a single detector or light source, respectively, may be used as desired.

In the two embodiments just described, as well as the other embodiments described, the light emitted from the light source 38 will likely be in a cone shape expanding away from the light source 38. Ideally the light source 38 is positioned in yoke 36 so that the central axis of this light "cone" will be perpendicular to the elongated axis of the drop chamber 22. Since FIGS. 11-14 show cross-sectional views of embodiments of the invention through the drop chamber 22, the central axis of the light "cone" will be in the plane of the drawing.

However, because the light "cone" is expanding as it moves away from light source 38, much of the light emitted from light source 38 will be emitted above and below the plane of the drawings of FIGS. 11-14. The detectors 40 heretofore described have been designed primarily to detect light at either a single point or along an axis parallel to the plane of the drawings of FIGS. 11-14. With these detectors, some of the light emitted from light source 38 will not impinge on detectors 40 and will therefore not be detected. Further, even light emitted from the light source originally in the plane of the drawings of FIGS. 11-14 may be refracted or reflected into paths diverging from this plane while passing through the walls of drop chamber 22 or while interacting with the drops themselves.

One solution to this problem is to expand the size of detector 40. For example, instead of a horizontal detector 40 as used in the embodiments of FIGS. 11 and 12, a detector 40 having a large vertical dimension in addition to the horizontal dimension could be used to detect light moving in paths divergent to the plane of the drawings.

Figure 14:
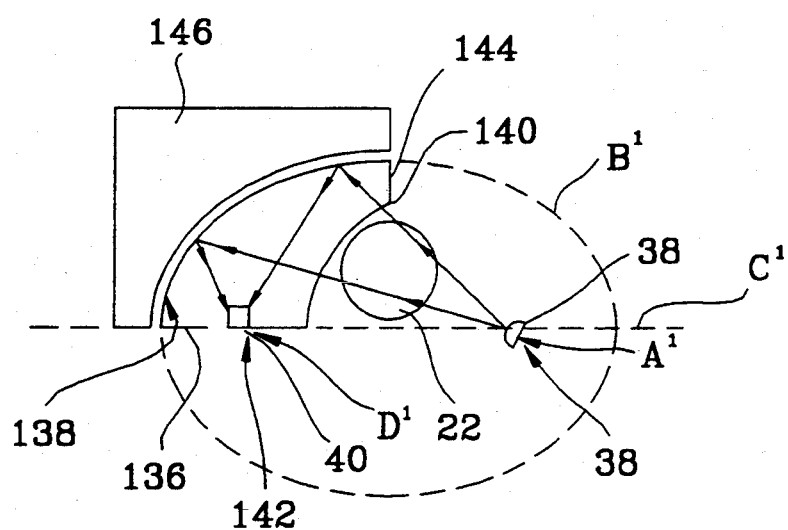
FIG. 14 is a cross-sectional view of another embodiment of the invention.
Figure 15:
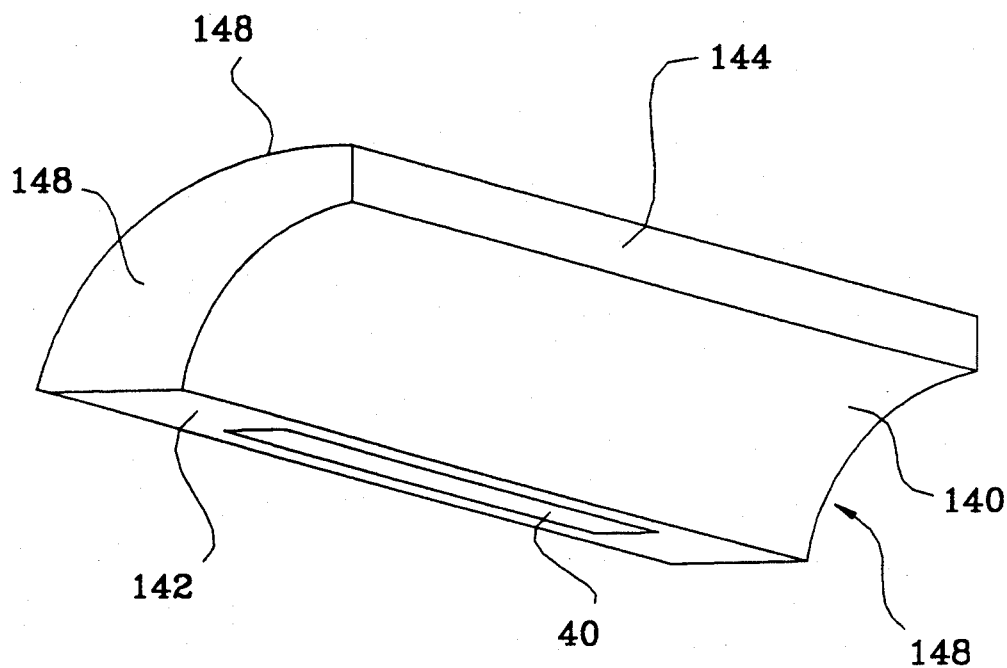
FIG. 15 is a perspective view of the light pipe of the embodiment shown in FIG. 14.

In the embodiments shown in FIGS. 13 and 14, the detector 40 could have a substantial dimension along the axis passing through the element labeled 40 and perpendicular to the plane of the drawing while still maintaining its small cross-sectional area at the focus D,D' of the ellipse B,B' respectively. With such a detector 40, light which is divergent to the plane of the drawing would still be focused along this elongated detector and would therefore be detected.

Another solution to the problem of detecting light emitted from light source 38 or diffracted by interaction with drop chamber 22 or drops therein, is to extend light pipe 136 above and below the plane of the drawing in Figure 14, terminate both ends 148 of light pipe 136 with a planar surface parallel to the plane of the drawing and coat these ends 148 with a reflective material. In this way, light diverging from the plane of the drawing will pass through inner surface 140 into light pipe 136. The light will be reflected off the reflective coating on outer surface 138 in a direction toward one of the ends of light pipe 136. The light will be reflected off the reflective coating on the ends of light pipe 136 back toward the plane of the drawing and toward detector 40 where it may be detected. This embodiment keeps the light within the light pipe where it has a greater chance of being detected than if the light were allowed to pass out of the light pipe through the ends of the light pipe.

As stated above, a possible problem with the embodiments shown in FIGS. 13 and 14, is that light impinging on inner surface 134 (FIG. 13) or outer surface 138 (FIG. 14) at a very acute angle to line C or C', respectively, will be reflected to detector 40 also at a very acute angle. Because detector 40 will typically have a flat surface for detecting, and in the embodiment of FIG. 11, because of the possibility of internal reflections off of surface 142, much light reflected toward detector 40 at a very acute angle will be difficult to detect.

Figure 16:
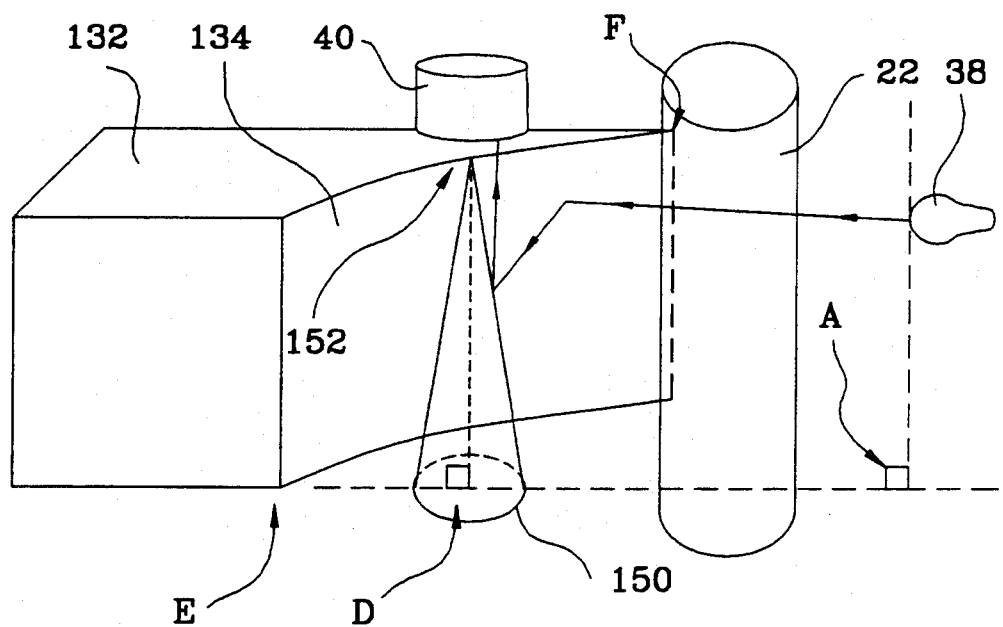
FIG. 16 is a perspective view of the embodiment of FIG. 13 with a cone placed at the second focal point.

To solve this problem, a reflective cone 150 (FIG. 16) may be used having its central axis perpendicular to the plane of the drawings of FIGS. 13 and 14 and centered on what is labeled detector 40. In this embodiment, detector 40 is moved to be located above the apex 152 of the cone and directed toward the cone 150. With this reflective cone, light approaching focus D or D' at an acute angle to line C or C', respectively, as well as all other light approaching focal points D,D' will be reflected off of the reflective surface of the cone 150 into detector 40. Virtually all the light impinging on detector 40 will strike the typically flat surface of detector 40 at a nearly perpendicular angle which increases the probability that the light will be detected.

In the embodiment shown in FIG. 13, the reflective cone 150 as described above could be placed at focal point D with detector 40 positioned by yoke 36 above and directed toward the apex of the reflective cone. In the embodiment of FIG. 14, a cone shaped recess could be cut into light pipe 136, oriented as described above. The surface of the cone should then be coated with a reflective coating so that light reflected off of outer surface 138 will then be reflected off of this reflective coating into detector 40. Again, in this embodiment, detector 40 would be located above and directed toward the apex of the reflective cone.

In all the embodiments disclosed herein, diodes 38 and detector 40 are preferably offset from the top portion 26 of the drop chamber 22 by a sufficient distance to allow drop formation from the drop formation area 32.

During the drop detection process, any ambient light that is present in drop chamber 22 may be detected by detector 40. The detection of this ambient light may affect the accurate detection of drops passing through drop chamber 22. It is therefore desirable to minimize the effect of ambient light on drop detection.

One way to minimize the effect of ambient light on drop detection is to minimize the amount of ambient light present in drop chamber 22. Since ambient light, by definition, comes from outside the drop chamber 22, drop chamber 22 is preferable surrounded and shielded by material opaque to the ambient light. In the invention, since diodes 38 and detector 40 preferably emit and detect infrared light, drop chamber 22 is preferable surrounded by material opaque to infrared light such as a polysolfone material. In this way, the residual ambient light present in drop chamber 22 is quite small.

An additional or alternate way to minimize the effects of ambient light on drop detection is to illuminate detector 40 by diodes 38 with sufficient intensity that detector 40 is saturated when no drop is passing between diodes 38 and detector 40. Because detector 40 is saturated, its resulting detector output signal will be at a constant relatively low negative voltage. At this relatively low voltage, the presence of ambient light cannot cause the detector 40 to produce a lower voltage detector output signal than is already being produced. Further, in the absence of any ambient light striking the detector 40, the detector 40 is already saturated and therefore producing its lowest voltage detector output signal.

In this condition, when a drop passes between diodes 38 and detector 40, some of the light emitted from diodes 38 will be blocked by the drop and consequently will not impinge on detector 40. This will cause detector 40 to move out of saturation and produce a detector output signal with a relatively higher voltage than the saturated level detector output signal.

Since detector 40 is no longer saturated, it is capable of detecting the presence of ambient light. The detected ambient light will cause the detector output signal from detector 40 to have a higher voltage during the passing of the drop through drop chamber 22 than it would have without the presence of the ambient light. However, the relative effect of ambient light on the detector output signal from detector 40 compared to the blocking effect of the passing drop is quite small.

For example, in a drop detection device made according to the teachings of the invention, if the saturation level of the detector output signal is −2 volts, a passing drop will block sufficient light from diodes 38 to typically cause about a 100–500 microvolt increase in the detector output signal. Where drop chamber 22 is surrounded by light blocking material as described above, at less than the saturation level, residual ambient light will cause the detector output signal to vary by about 1–10 microvolt. In this case, the effect of the passing drop on the detector output signal is at a minimum about 10 times more than the effect of the ambient light.

Even without the blocking material described above the effect of the passing drop is larger than the effect of ambient light in all but the most severe cases. For example, as above where the saturated voltage level of the detector output signal is −2 volts and a passing drop causes a 100–500 microvolt increase in the detector output signal voltage, the unshielded ambient light will typically produce about a 50 microvolt variation in detector output signal strength.

As described above, as the drops fall or slide through the drop chamber 22, they block some of the light passing from diodes 38 to detector 40. When detector 40 is illuminated in a saturated mode, the passing of drops through the drop chamber 22 causes the detector Output signal from detector 40 to increase. Further, a high tilt angle of the drop chamber 22 and varying ambient light conditions makes the changes in detected light actually caused by the drops to be difficult to detect with detector 40. To compensate for these conditions and to correctly identify and count the drops falling through the drop chamber 22, detector 40 is preferably connected to a drop detection circuit 21, schematically illustrated in FIG. 3.

Drop detection circuit 21 filters out any unwanted portions of the detector output signal, amplifies the remainder of the signal which is presumably caused by drop flow and detects the appropriate condition of the detector output signal corresponding to a drop passing through the drop chamber. The microprocessor 14 processes the detector output signal operated on by drop detection circuit 21 to determine the flow rate and to determine if proper flow is occurring. Microprocessor 14 uses the determined information to control pump 17 and display pertinent information on display 16.

Figure 3A:
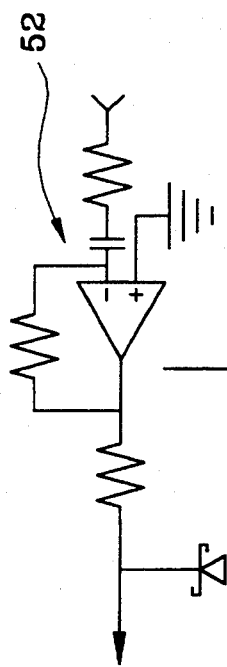
FIG. 3 is a circuit schematic diagram showing a drop detection circuit according to invention.
Figure 3:
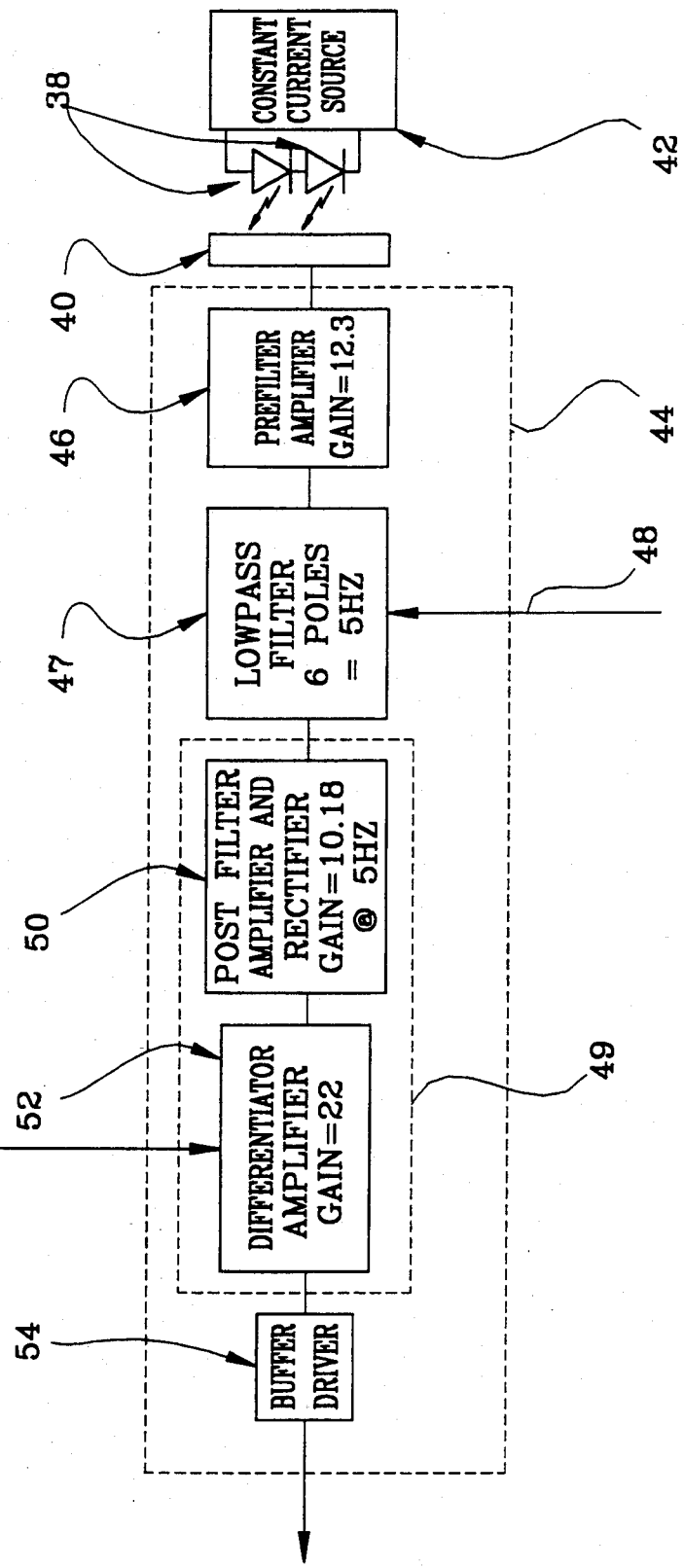

The drop detection circuit 21 shown in FIG. 3 includes a driver circuit 42 that powers the two IRLEDs 38 and preferably provides a constant current supply to the IRLEDs 38 to maintain constant optical output. Any variation in the optical output would add unwanted signals to the detector output signal, so constant optical output is important. A detector circuit 44 receives the detector output signal from detector 40 and converts it to a signal indicating whether or not a drop is flowing.

The detector circuit 44 includes a prefilter differentiator amplifier 46. Prefilter amplifier 46 amplifies the signal from the detector 40. As stated, when no drop is passing through drop chamber 22, detector 40 is saturated and the corresponding detector output signal presented to prefilter amplifier 46 is a constant signal of relatively high voltage. Drop passage through drop chamber 22 manifests itself as an increase and subsequent decrease back to the saturation level of the detector output signal. Consequently, it is this variation from the saturation level detector output signal that is to be detected.

As shown above, the variation in detector output signal level from drop passage is relatively small compared to the saturated detector output signal level. If the entire signal were amplified to a level to accentuate the variation in the detector output signal resulting from drop passage, the resulting signal would saturate most amplifiers. Therefore, it is desirable to amplify only the varying or AC part of the detector output signal.

This is accomplished at prefilter amplifier 46 by using an inverting differentiating amplifier that effectively blocks the DC component and amplifies the varying or AC component of the detector output signal. The inverting differentiating amplifier produces an inverted wave output signal that goes negative when the saturation detector output signals goes positive relative to the saturated level detector output signal. This results in a rough sinusoidal wave signal having a fundamental frequency the same as the frequency of drop formation as will be explained hereafter. The signal output from prefilter amplifier 46 is passed to a low pass filter 47.

Filter 47 is a switched capacitor 6 pole low pass filter, preferably a National Semiconductor Corporation LMF60-100. Filter 47 removes frequency components on the detector output signal corresponding to artifacts, including ambient light artifacts, while passing the frequency components of the detector output signal corresponding to the passing of drops through the drop chamber 22. Although the input to filter 47 is roughly a sinusoidal wave, as a result of the filtering operation, the/output of filter 47 is improved sinusoidal centered around zero volts so that both positive and negative parts of the sinusoidal signal are present.

As stated above, in the preferred embodiment of the invention, at flow rates less than 100 ml/hour, the rotor 18 will rotate for ⅓ revolution, so that one roller 19 rolls over the tube 24, and then pause before the next ⅓ rotation of the rotor 18. At flow rates greater than 100 ml/hour, rotor 18 turns for a complete revolution before pausing before the start of the next revolution.

The frequency components of the detector output signal, corresponding to drops passing through the drop chamber 22, are directly related to the rate of drop formation. As described above, two or more drops, depending on the fluid used and the flow rate, are formed per "cycle". During operation, the pump rotor 18 turns for either ⅓ or a full revolution, depending on the flow rate, and then pauses for a wait time J before continuing to rotate for the next ⅓ or full revolution. The time length of a "cycle" (J+K) is controlled by microprocessor 14 based on the flow rate so that the length of the pause (time J) varies depending on the flow rate. However, despite the length of the pause, While rotor 18 is turning, it turns at a constant speed so that the length of time K for each ⅓ or full revolution is constant for the corresponding flow rate. Of course, the longer the pause (time J) between drop production, the fewer drops per the time (J+K) of a "cycle" are formed and the lower the flow rate.

As stated above, the speed of rotation of rotor 18 is constant so that the number of drops formed per ⅓ or full rotation is constant at each flow rate. The variation in the detector output signal is directly related to the drops passing through the drop chamber 22.

Drops are formed as the rotor 18 rotates and forces fluid through the drop formation area 32 in drop chamber 22. The drop formation occurs during each ⅓ or full revolution. Thereafter there will be a pause in drop production as rotor 18 ceases to rotate after the completion of one ⅓ or full revolution and before the beginning of the next "cycle". As a result, the detector output signal reflects the formation and passing of the drops through the drop chamber 22 and the subsequent absence of drops formed and passed through drop chamber 22 as a result of the rotation of the rotor 18 during a "cycle".

As stated above, in the preferred embodiment of pump 17, the rate of rotation of rotor 18 is about ½ complete rotations per second, or about 30 R.P.M. The rotor 18 typically has three rollers 19 so there are three drop formation times (corresponding to time K) per complete rotation of rotor 18. The time length (J+K) of a "cycle" varies from about 3 seconds at a flow rate of 400 ml/hour to several minutes at the lowest flow rates.

At low flow rates, each "cycle" includes ⅓ revolution of rotor 18 and produces 2 to 4 drops. At flow rates of 100 ml/hour and above, each "cycle" includes a complete revolution of rotor 18 and produces a minimum of 4 drops and more typically about 6 drops. Therefore, the detector output signal has a frequency components from about zero (0) Hz. to about three (3) Hz. Variations having frequencies significantly above this frequency are the result of artifacts including variations in ambient light. Consequently, lowpass filter 47 has a $-3$ dB cutoff frequency of about 5 Hz. to filter out components of the detector output signal significantly above this maximum drop frequency. The $-3$ dB cutoff frequency of 5 Hz. is chosen to optimize the filtering of artifacts of higher frequency than the expected drop frequency components, and also allows detection of drops falling at a slightly higher than expected rate.

As stated, lowpass filter 47 is preferably a switched capacitor filter. Consequently, filter 47 requires an input frequency to regulate the switching of the capacitors. Therefore, microprocessor 14 sends an input clock signal to filter 47 on line 48 that causes lowpass filter 47 to vary its cut-off frequency in response to the input clock signal 48. In the preferred embodiment, the input clock signal input on line 48 is a 534 Hz. signal and filter 47 divides the input clock signal by 100 to derive a cutoff frequency of 5.34 hz.

The combination of prefilter amplifier 46 and filter 47 produces an output signal having frequency components from about zero (0) Hz. to about 5.34 Hz. The fundamental frequency of drop production will dominate the other remaining frequency components so the signal output from filter 47 will almost entirely be an approximately symmetrical sinusoidal signal at the instantaneous drop production frequency.

The signal traces labeled "L" in FIGS. 17–32 show typical detector output signals for various fluids and conditions of the drop chamber 22 after being amplified by prefilter amplifier 46 and passed through low pass filter 47. In FIGS. 17–28, the infusion device 10 is operating normally and the tube 24 below the bottom portion 28 is not blocked. In FIGS. 29–32 the tube 24 below the bottom portion 28 is occluded.

In FIGS. 17, 20, 23, 24, 29 and 30, drop chamber 22 is vertical as it is positioned in yoke 36. In FIGS. 18, 21, 25 and 31, drop chamber 22 is tilted to the left of a line extending from diodes 38 to detectors 40 when viewed from diodes 38. In FIGS. 19, 22, 26 and 32, drop chamber 22 is tilted to the right of a line extending from diodes 38 to detectors 40 when viewed from diodes 38.

It has been found that the detection of drops passing through drop chamber 22 is most difficult when drop chamber 22 is tilted to the left or right, as described above, as compared to when drop chamber 22 is vertical in yoke 36 or when drop chamber 22 is tilted toward or away from diodes 38. Experience has shown that drops can be detected passing through drop chamber 22 when drop chamber 22 is tilted up to 80° toward or away from diodes 38. However, drops passing through drop chamber 22 when drop chamber 22 is tilted to the left and right, as described above, can reliably be detected only when drop chamber 22 is tilted less than about 55°.

Figure 26:
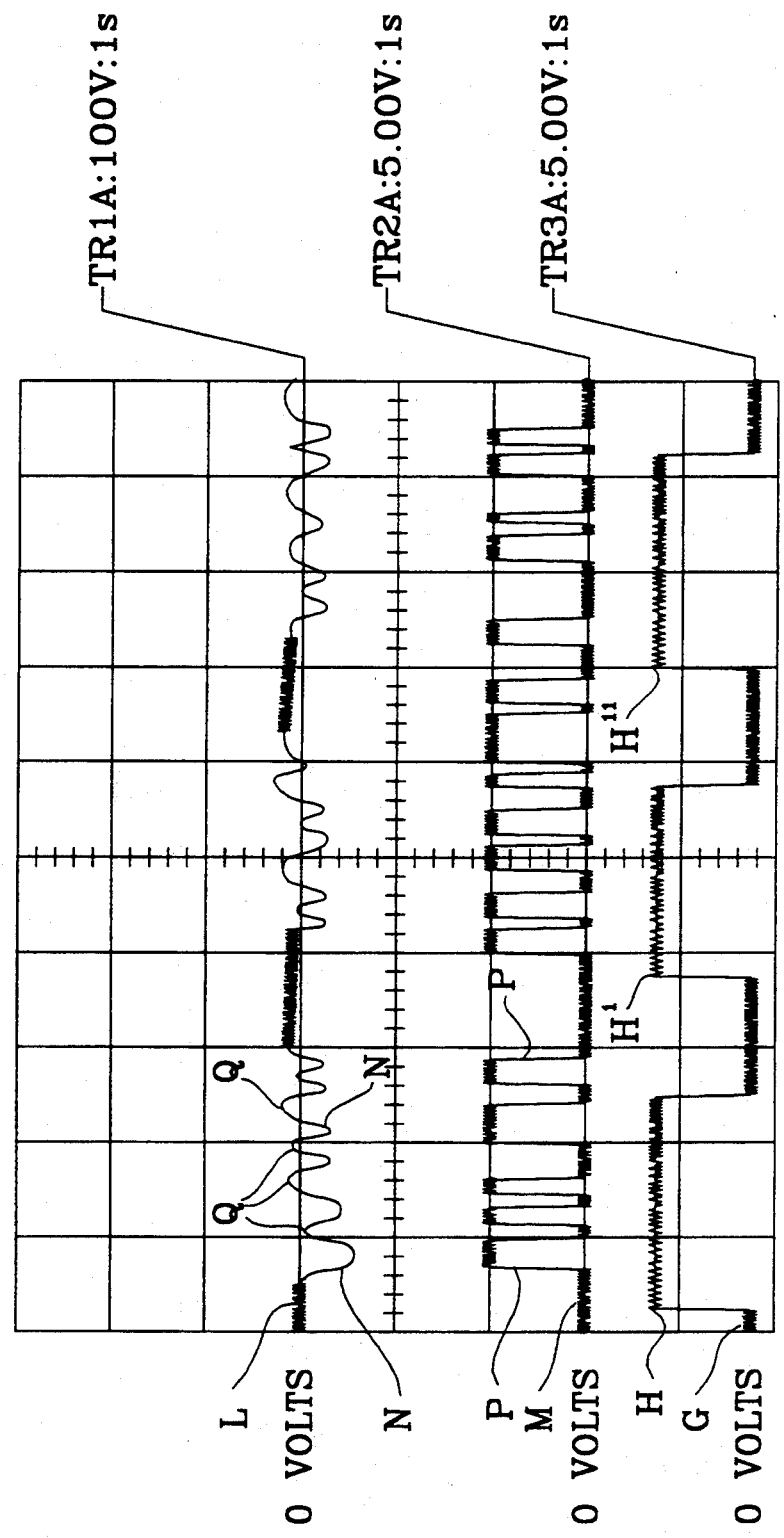
FIG. 26 is a trace of the output of the invention at points L and M in FIG. 3 when the invention is pumping water at a flow rate of 400 ml/hour and at a 50° tilt to the right relative to the central axis of the drop chamber and a trace of the pump motor control signal.
Figure 27:
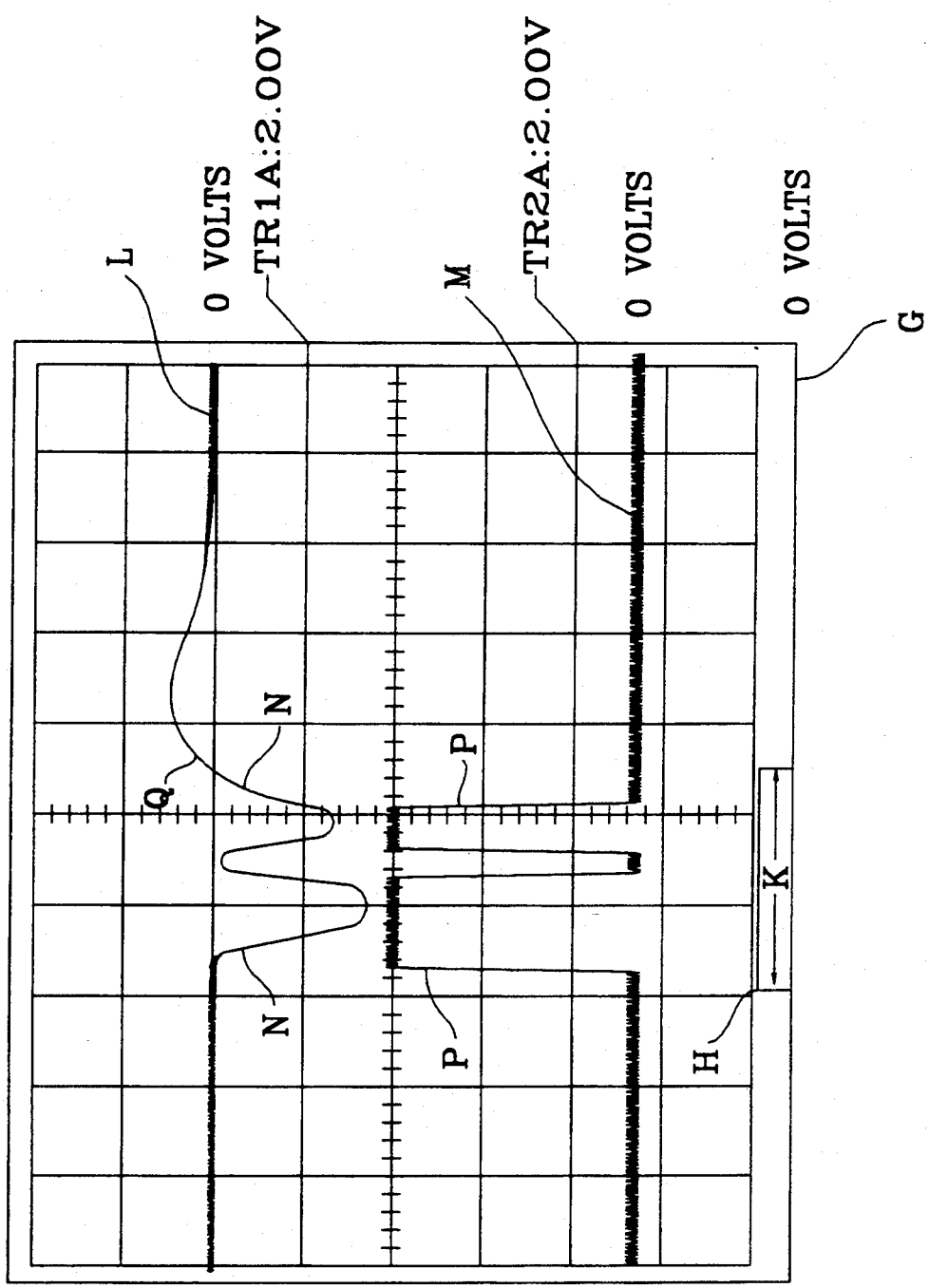
FIG. 27 is a trace of the output of the invention at points L and M in FIG. 3 when the invention is pumping Pre-Attain ® at a flow rate of 95 ml/hour and at a 45° tilt angle to the left relative to the central axis of the drop chamber and a trace of the pump motor control signal.
Figure 28:
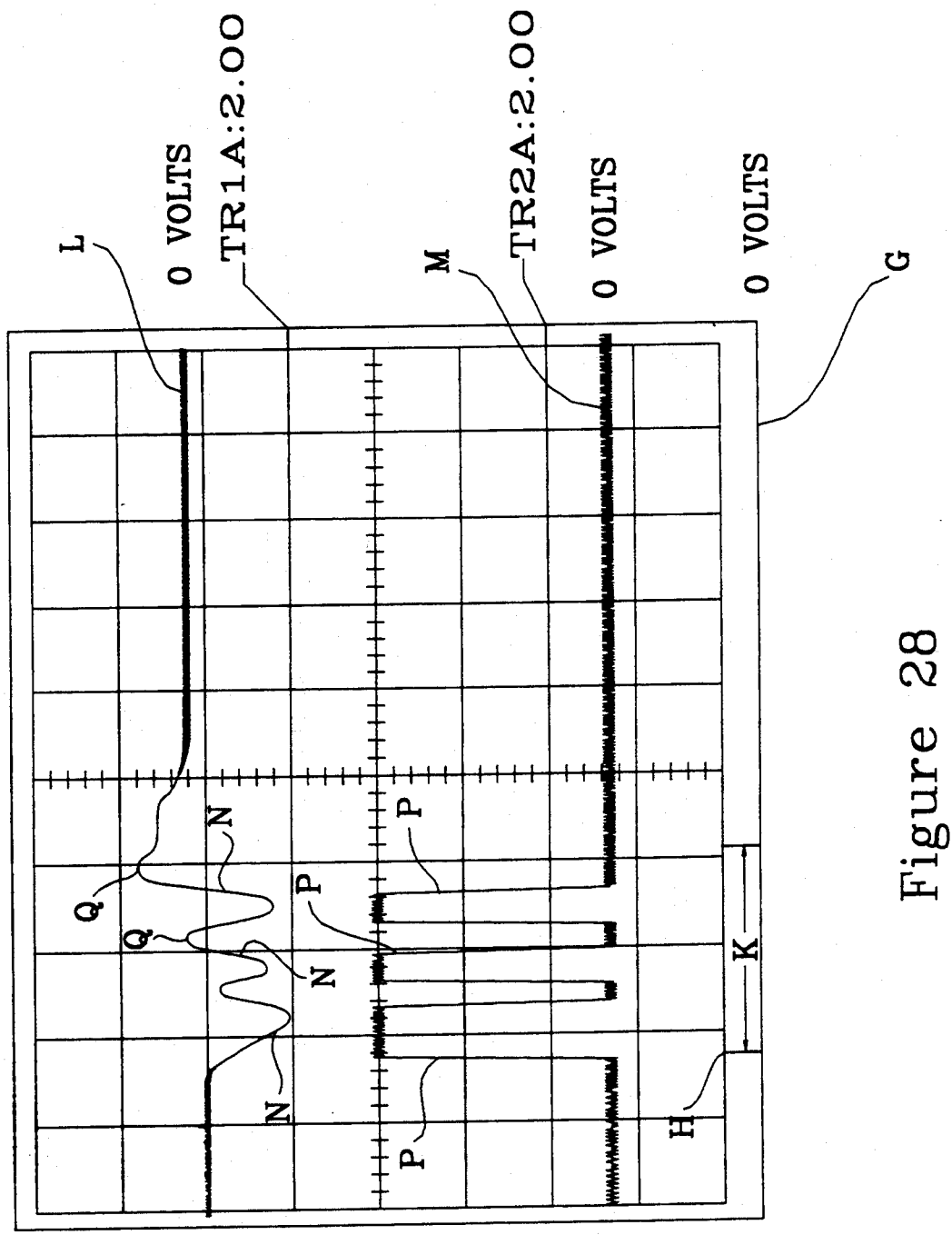
FIG. 28 is a trace of the output of the invention at points L and M in FIG. 3 when the invention is pumping Pre-Attain ® at a flow rate of 95 ml/hour and at a 0° tilt angle relative to the central axis of the drop chamber and a trace of the pump motor control signal.

In FIGS. 18, 19, 21, 22, 25, 26, 31 and 32, despite the severe angles of tilt of the drop chamber 22 of the devices 10, a minimum of two (2) drops are formed and detected per "cycle". In FIGS. 26–28, the tube below the bottom portion 28 is occluded. Here, only a single drop is formed and detected per "cycle" as will be explained hereafter.

After amplification and filtering, the signals are passed to a differentiator circuit 49. Differentiator circuit 49 includes a post filter amplifier 50, including a rectifier, and a differentiator amplifier 52.

Since the saturation level of the detector output signal is a negative DC signal that is removed by prefilter amplifier 46, the signal from lowpass filter 47 when no drop is passing through the drop chamber 22 at point L will be at zero volts. When a drop passes through drop chamber 22, the resulting detector output signal will be more positive than the constant negative DC voltage so the differentially amplified and filtered signal at L will be a sinusoidal signal centered on zero volts having a frequency the same as the drop production frequency.

First, post filter amplifier 50 amplifies the output of filter 47 including removing any D.C. offset. The rectifier of post filter amplifier 50 then removes the positive "half" of the sinusoidal signal at L leaving the negative "half" of the sinusoidal signal. The remaining negative "half" of the sinusoidal signal corresponds to the positive going detector output signal caused by the drops passing through drop chamber 22. The resulting signals are then passed from post filter amplifier 50 to differentiator amplifier 52.

Differentiator amplifier 52, as shown in FIG. 3a, is a conventional differentiator circuit preferably using an op-amp. The purpose of differentiator amplifier 52 is to detect the falling edge of the signal output from post filter amplifier 50 with a slope above a threshold value and produce an amplified square wave output as long as the negative slope of the signal exceeds the threshold value. The amplified square wave output is only produced while negative going signal has a slope above a specific threshold value.

Figure 17:
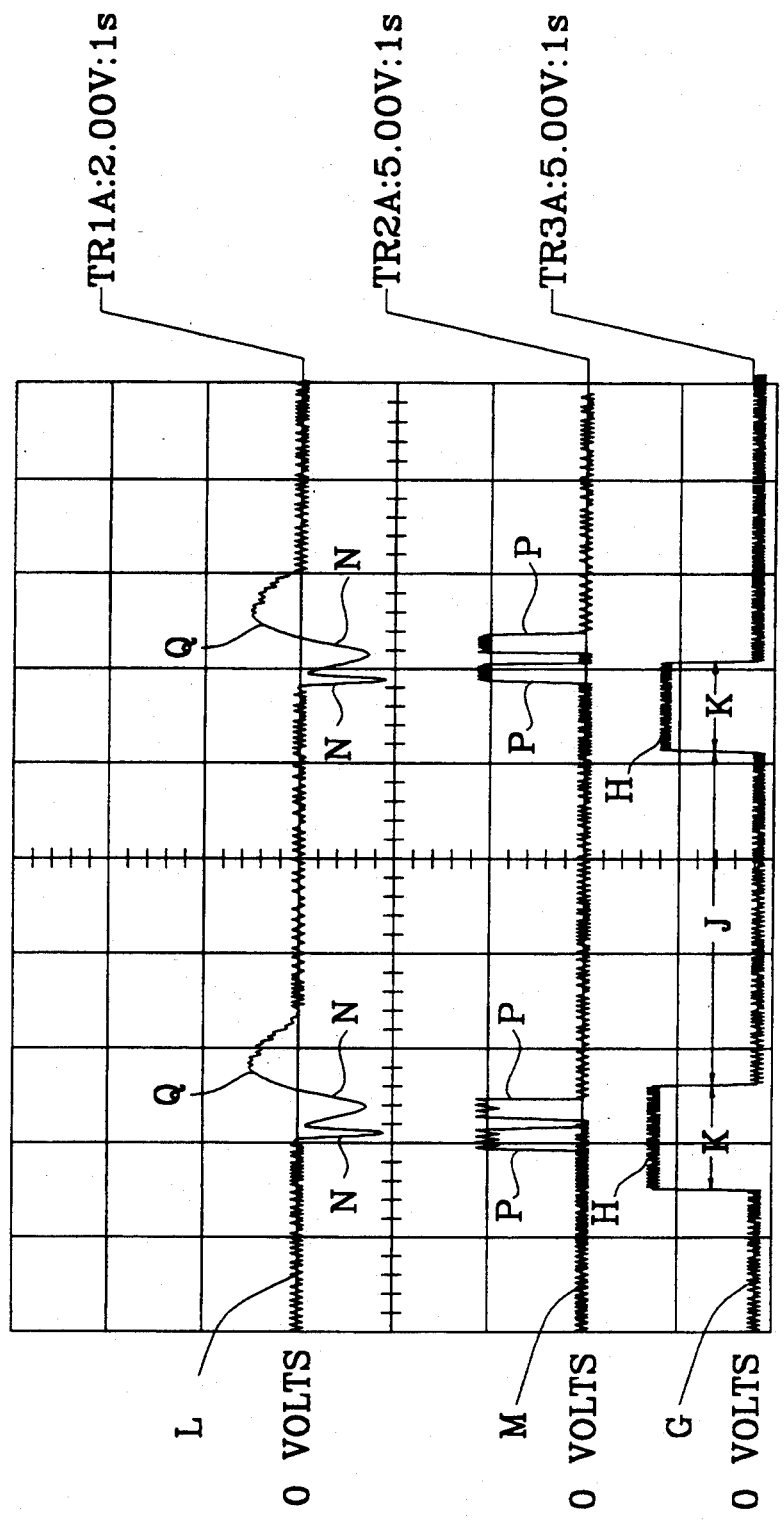
FIG. 17 is a trace of the output of the invention at points L and M in FIG. 3 when the invention is pumping water at a flow rate of 95 ml/hour and at a 0° tilt angle relative to the central axis of the drop chamber and a trace of the pump motor control signal.

As discussed above, the signal output from filter 47, labeled "L", includes positive sinusoidal elements such as that labeled Q in FIG. 17 that result from the filtering process. It is possible that the slope of the positive signal Q as it returns to zero volts from its peak positive voltage could exceed the threshold value of differentiator amplifier 52. If signal "L" where passed to differentiator amplifier 52 without first passing through post filter amplifier 50, the negative going slope of signal Q could cause a corresponding square wave output. However, this square wave would result as an artifact of the filtering process and not as a result of a drop passing through drop chamber 22. Therefore, the rectifier of post filter amplifier discussed above removes or "clips" the positive elements such as Q to remove the possibility of generating a square wave that does not correspond to a drop passing through drop chamber 22.

The optimum threshold value for the slope has been found to be about 0.45 volts/second. This threshold valve has been found to correspond to the detector output signal produced by drops passing through the drop chamber signals having slopes with values lower than the threshold value the drop chamber 22 and consequently are "filtered" from the signal by differentiator amplifier 52.

The signal output from differentiator amplifier 52 passed to buffer driver 54. Buffer driver 54 buffers the output signal from differentiator circuit 49 before passing the signal to microprocessor 14 for further processing.

The effect of differentiator circuit 49 on the signals is illustrated in FIGS. 17-32 in the trace labeled M. As stated above the upper waveform, labeled "L", represents typical outputs of the low pass filter 47 at point L, which is input to the post filter amplifier, rectifier and ultimately to the differentiator circuit 49. The middle waveform, labeled "M", represents the output of differentiator circuit 49, through a buffer driver 54, at point M.

For microprocessor 14 to consider signals from the drop detection circuit 44 as representing a valid drop, the amplified and filtered detector output signal presented to differentiator amplifier 52 must have a falling edge with a slope above a threshold value, found optimally to be about 0.45 volts per second. It has also been found that when the sequential drops formed at the drop formation area 32 per "cycle" pass through the drop chamber 22, their individual detection by detector 40 is overlapped so that a composite "W" shaped signal, such as is shown in FIG. 17, is formed.

However, even in the composite signal representing overlapping drop detection, the threshold voltage slope corresponding to each drop passing through drop Chamber 22 is preserved. It is for this reason that the slope of the detector output signal is sensed to determine the drop count as opposed to sensing the voltage drop in the detector output signal. As a result, as shown in FIG. 17, the signal labeled M is a square wave output from differentiator amplifier 52 for each individual drop of the overlapping "W" shaped signal of trace L.

Occasionally, the patient end of the enteral feeding tube 24 becomes plugged or "occluded" so that fluid pumped by the pump 17 does not pass through the enteral feeding tube 24 into the patient 11. It is desirable for the pump 17 to sense this condition, cease pumping and render an alarm to alert the appropriate health care worker.

Initially, as the enteral feeding tube 24 becomes occluded, the pump 17 will continue to pump fluid through the drop chamber 22 into the enteral feeding tube 24. Because the feeding tube 24, drop chamber 22 and tube 24 above top portion 26 of drop chamber 22 are a gas and fluid tight system, as the fluid is pumped into the feeding tube 24, the feeding tube 24 will become filled with fluid.

Because the pump 17 is still pumping fluid into the feeding tube 24 through the drop chamber 22, the pressure in drop chamber 22 will increase. When the pressure increases sufficiently, although the rotating rollers 19 will be pushing fluid through drop formation area 32, the pressure within drop chamber 22 will be sufficiently high to prevent drops from forming and separating from drop formation area 32.

As a result, while the rotating roller 19 is pushing the fluid through the drop formation area 32, a pseudo-drop is formed a drop formation area 32. This pseudo-drop extends away from the drop formation area 32 into drop chamber 22 into the area between diodes 38 and detector 40. Because the pseudo-drop extends into the area between diodes 38 and detector 40, it blocks some of the light emitted from diodes 38 and is therefore detected by detector 40.

However, because of the high pressure within drop chamber 22, this pseudo-drop will not break free from the drop formation area 32. Instead, when the rotor 18 stops rotating so that the roller 19 is no longer pushing fluid through the drop formation area 32, the pressure within the drop chamber 22 pushes the pseudo-drop back into the drop formation area 32.

The detection signal for this pseudo-drop is shown in FIGS. 29-32. As can be seen, as the pseudo-drop is formed it blocks light emitted from diodes 38 causing the signal output from detector 40 to decrease. In many cases, the slope of the voltage drop produced by the pseudo-drop is above the threshold slope of 0.45 volts per second so that initially the microprocessor recognizes the pseudo-drop as an actual drop.

However, as stated above, the microprocessor 14 expects to detect at least two (2) drops per "cycle" at low flow rates and at least four (4) drops per "cycle" at higher drop rates. Further, since microprocessor 14 controls the rotation of rotor 18, microprocessor 14 knows when the rotor 18 is rotating and consequently when to expect to detect the resulting drops produced at drop formation area 32 by the rotation of rotor 18. Consequently, as rotor 18 rotates through a "cycle" and microprocessor 14 detects what appears to be a drop, depending-of the designated flow rate, at least one more drop at low flow rates and at least three more drops at high flow rates should be produced and detected before the next "cycle" is begun. If the expected number of drops are not detected for a requisite number of "cycles", an occlusion is most probably occurring. Therefore, pump 17 stops pumping and an alarm sounds.

Figure 18:
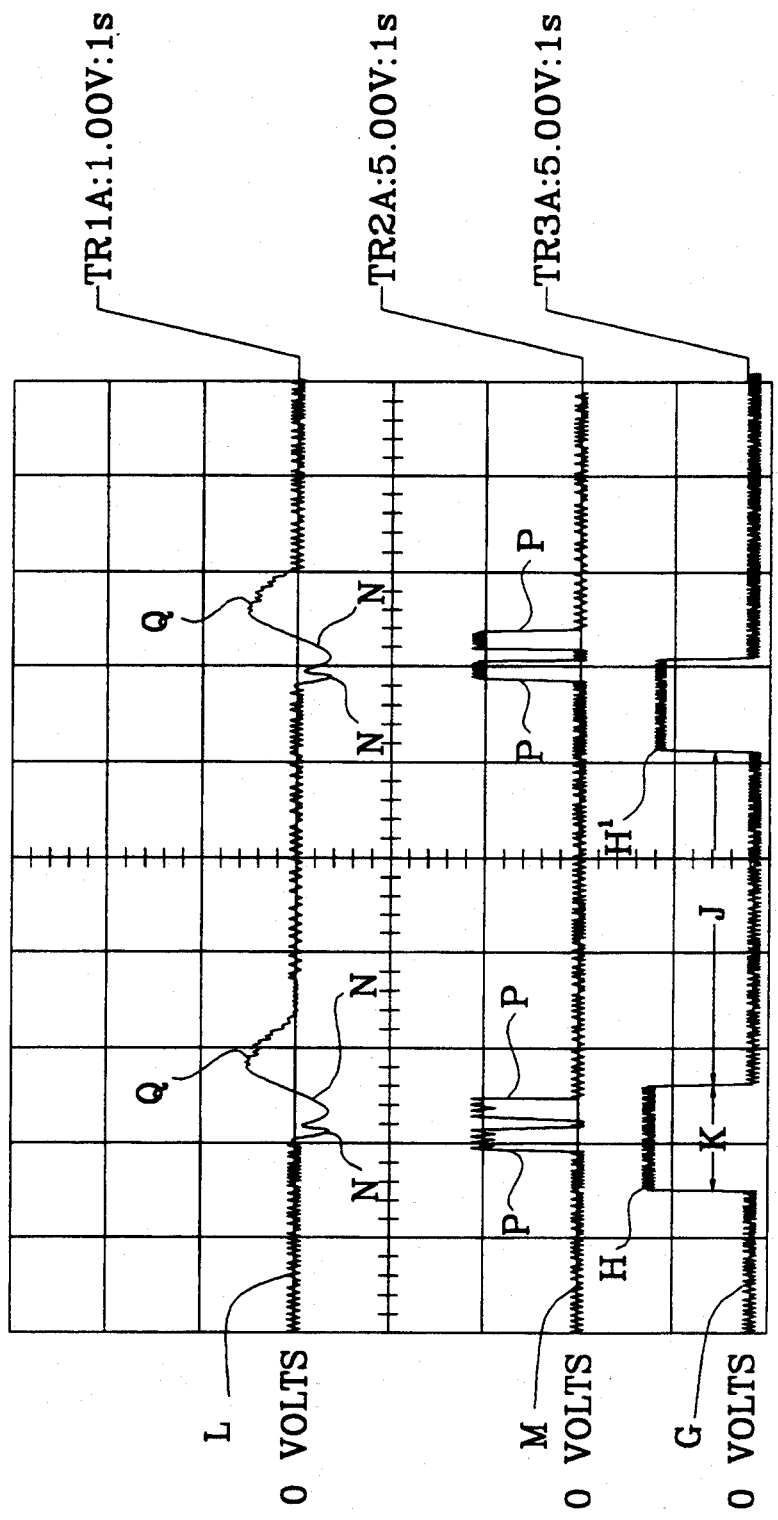
FIG. 18 is a trace of the output of the invention at points L and M in FIG. 3 when the invention is pumping water at a flow rate of 95 ml/hour and at a 50° tilt angle to the left relative to the central axis of the drop chamber and a trace of the pump motor control signal.
Figure 19:
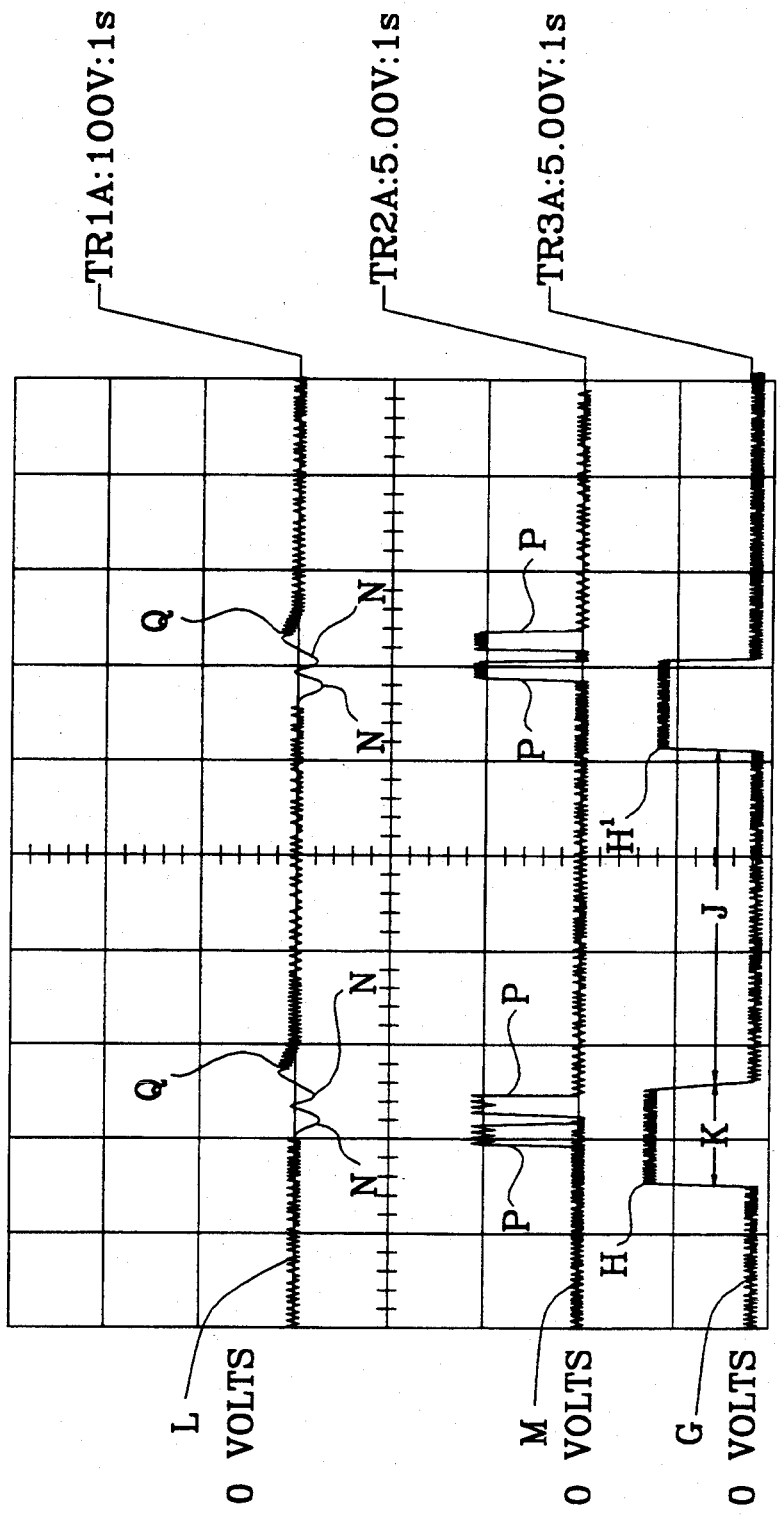
FIG. 19 is a trace of the output of the invention at points L and M in FIG. 3 when the invention is pumping water at a flow rate of 95 ml/hour and at a 50° tilt angle to the right relative to the central axis of the drop chamber and a trace of the pump motor control signal.

FIGS. 17, 18 and 19 show the signal output at points L and M for one "cycle" of the pump 17 pumping water at a flow rate of 95 ml/hour. In FIGS. 18 and 19 the/-drop chamber 22 is tilted 50 degrees to the left and right of the area connecting the diodes 38 and detector 40, respectively, while in FIG. 17, drop chamber 22 is not tilted. As can be seen, one "cycle" produces two drops at L and correspondingly, two amplified square wave signals at M.

As FIG. 17 clearly shows, the two drops passing through drop chamber 22 produce a detector output signal at L where each drop's individual contribution to the detector output signal is superimposed on the other drop's individual contribution to the detector output signal to produce a composite "W" shaped signal. The composite signal in this case has two "lobes" labeled N. Each of these "lobes" N has a downward slope above the threshold value so that two square wave signals P, corresponding to the detection of the downward slope above the threshold value are generated. The square wave signals P are sensed by microprocessor 14 to determine whether the correct-number of drops are sensed per "cycle".

Traces of the signal output at points L and M for the device 10 with drop chamber 22 at both the vertical and tilted angles corresponding to the orientation of drop chamber 22 in FIGS. 17 through 19 but at flow rates less than 95 ml/hour produce similar looking traces. The difference in the traces being that at low flow rates, the amplitude of the detected peaks is lower and the width of the peaks is wider. Further, because the lower flow rates are caused by a longer wait after rotor 18 rotates for ⅓ revolution before the next beginning of the ⅓ rotation, the spacing between peaks is greater at lower flow rates than it is at the 95 ml/hour flow rate. In all other respects, including the relative location of the negative slopes above the threshold slope, the traces for flow rates less than 95 ml/hour are like the corresponding traces shown in FIGS. 17 through 19.

Figure 20:
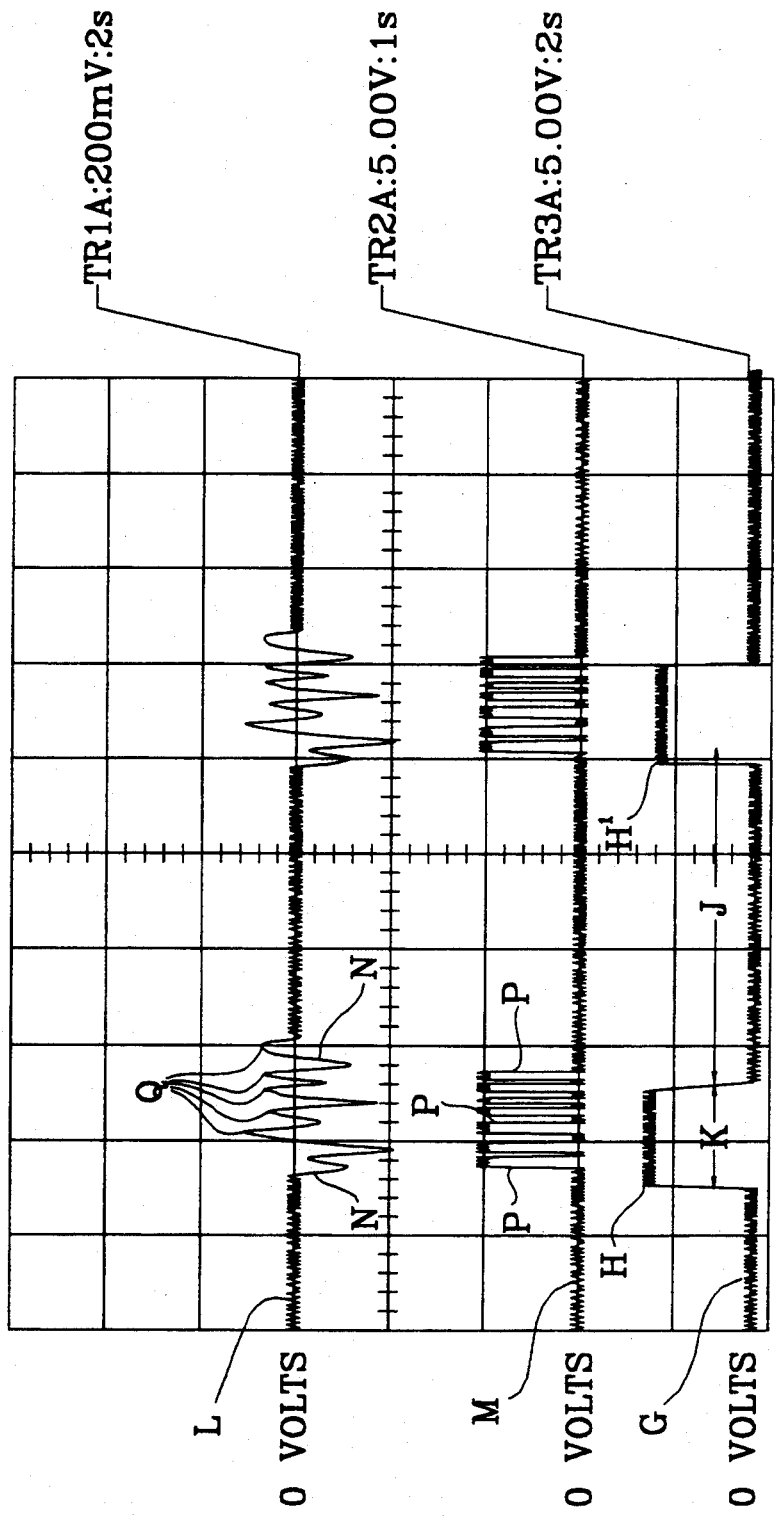
FIG. 20 is a trace of the output of the invention at points L and M in FIG. 3 when the invention is pumping water at a flow rate of 125 ml/hour and at a 0° tilt relative to the central axis of the drop chamber and a trace of the pump motor control signal.
Figure 21:
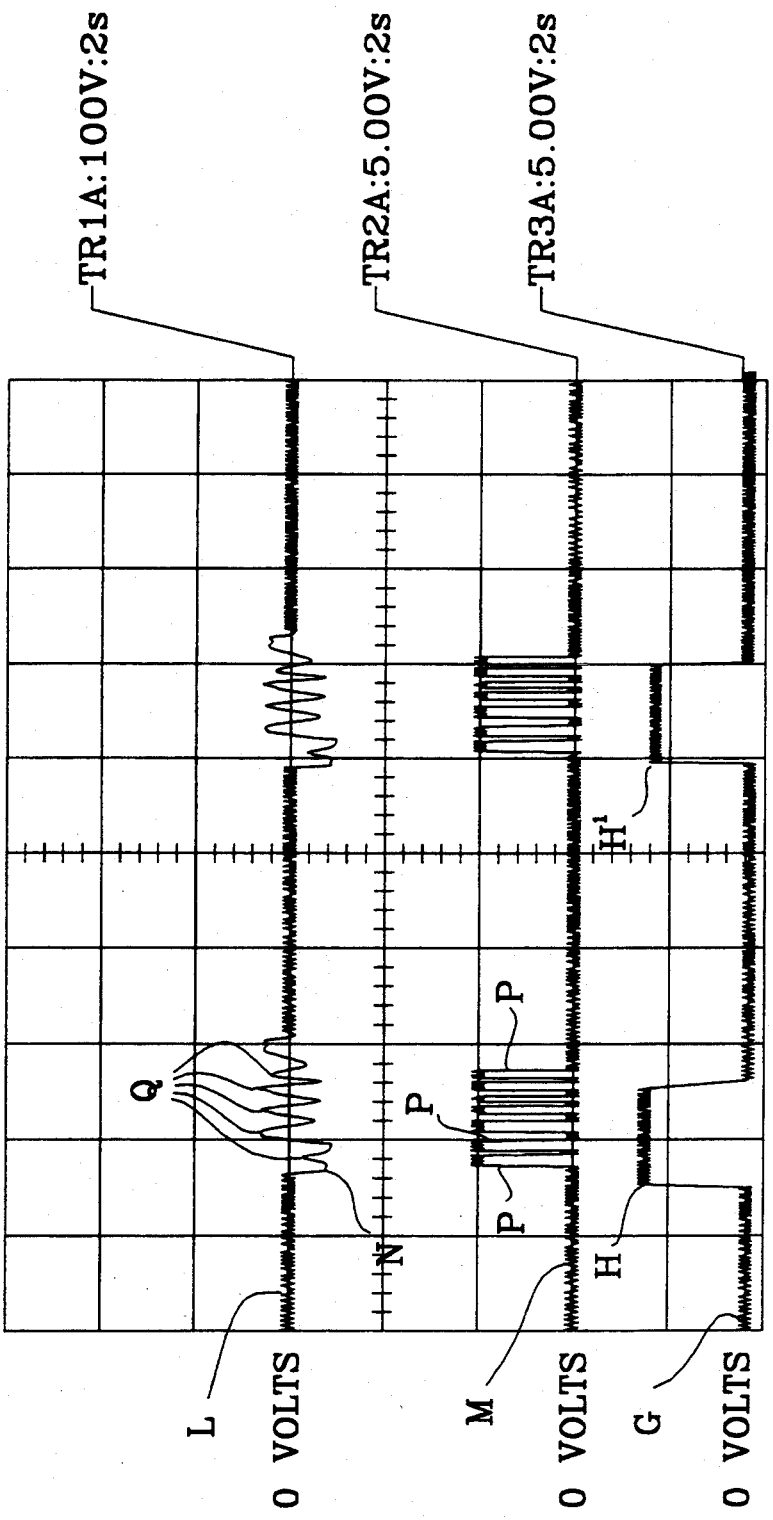
FIG. 21 is a trace of the output of the invention at points L and M in FIG. 3 when the invention is pumping water at a flow rate of 125 ml/hour and at a 50° tilt angle to the left relative to the central axis of the drop chamber and a trace of the pump motor control signal.
Figure 22:
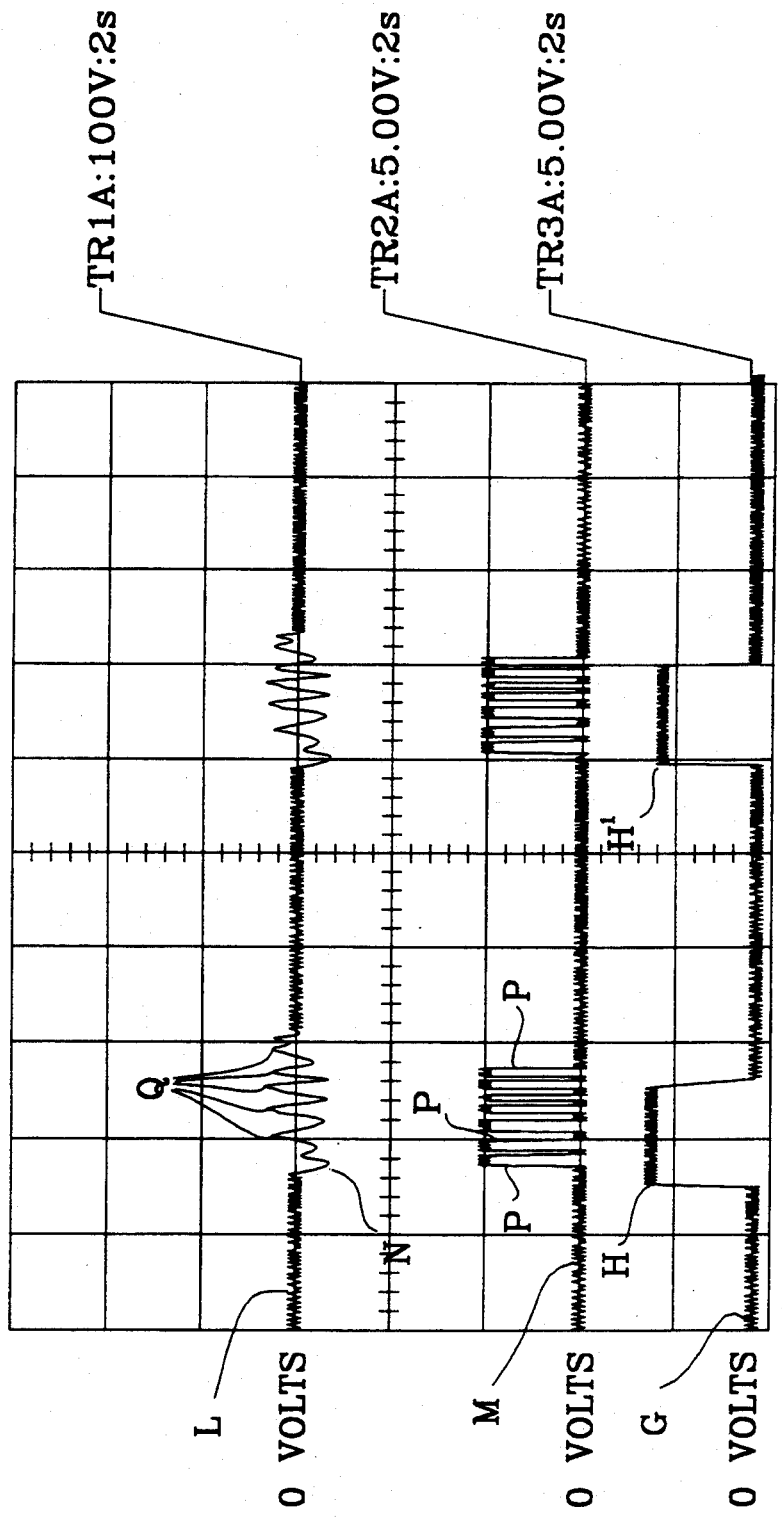
FIG. 22 is a trace of the output of the invention at points L and M in FIG. 3 when the invention is pumping water at a flow rate of 125 ml/hour and at a 50° tilt angle to the right relative to the central axis of the drop chamber and a trace of the pump motor control signal.
Figure 23:
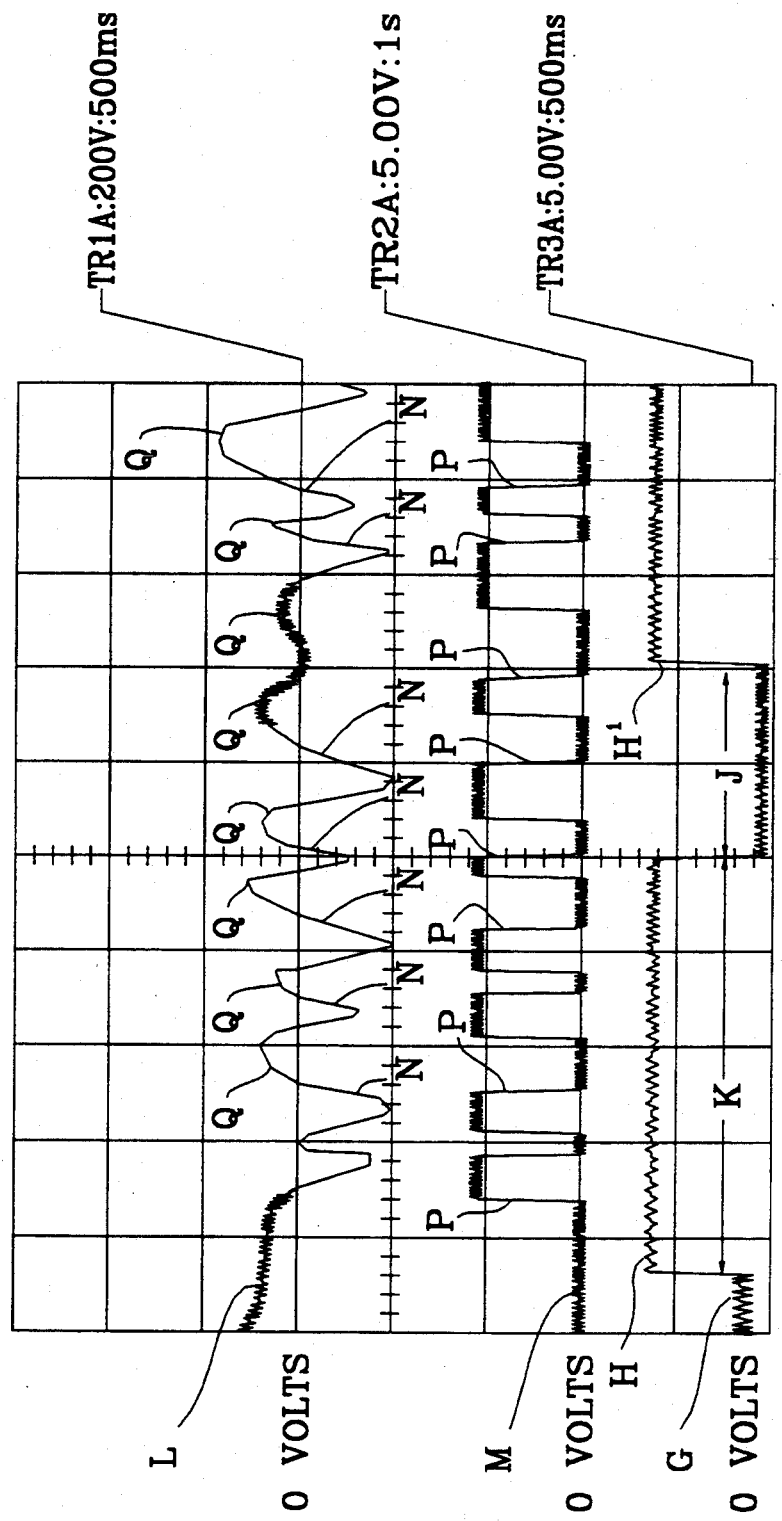
FIG. 23 is a trace of the output of the invention at points L and M in FIG. 3 when the invention is pumping water at a flow rate of 400 ml/hour and at a 0° tilt relative to the central axis of the drop chamber with a first time scale for the x axis and a trace of the pump motor control signal.
Figure 24:
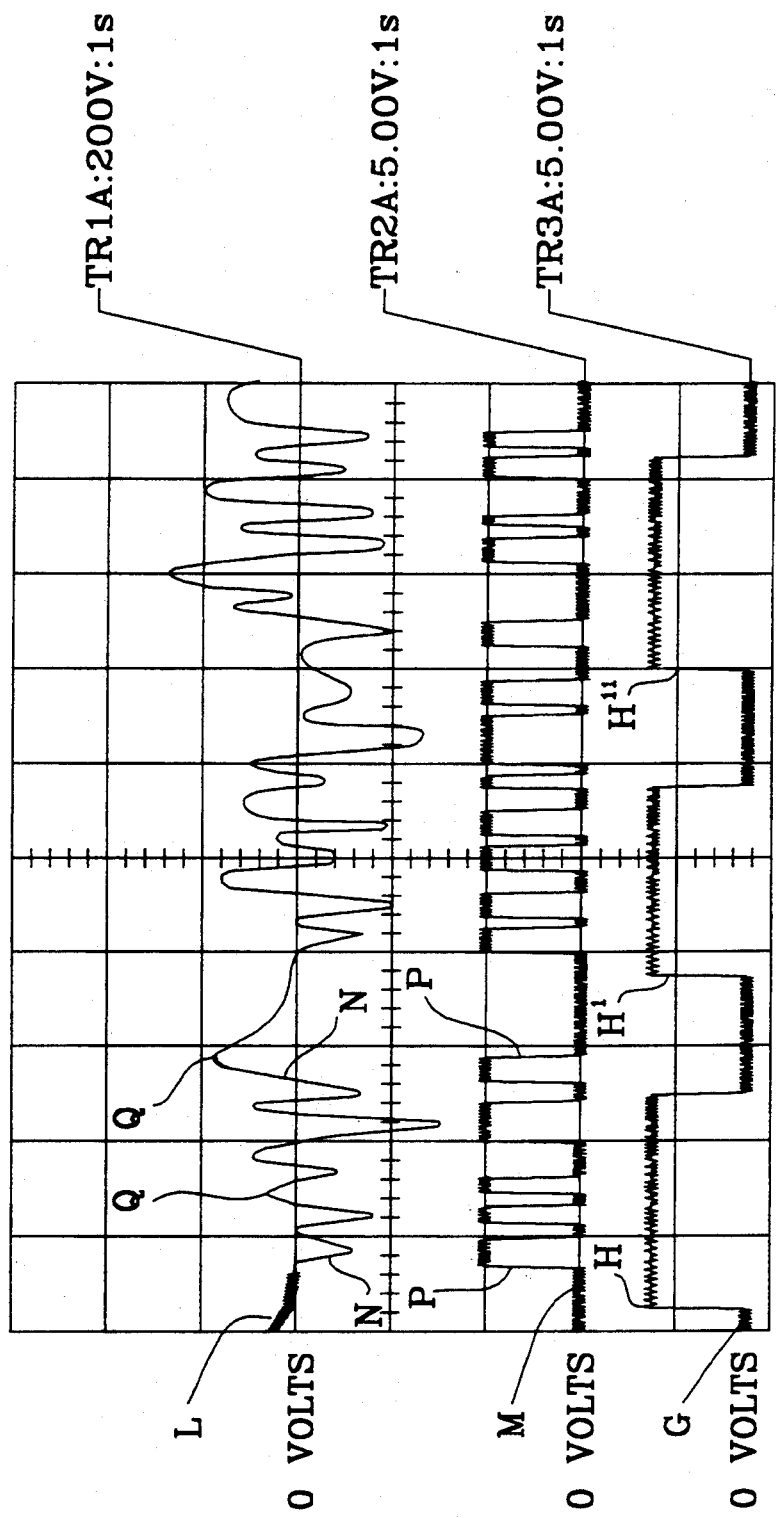
FIG. 24 is a trace of the output of the invention at points L and M in FIG. 3 when the invention is pumping water at a flow rate of 400 ml/hour and at a 0° tilt relative to the central axis of the drop chamber with a second time scale for the x axis longer than the first time scale of FIG. 23 and a trace of the pump motor control signal.
Figure 25:
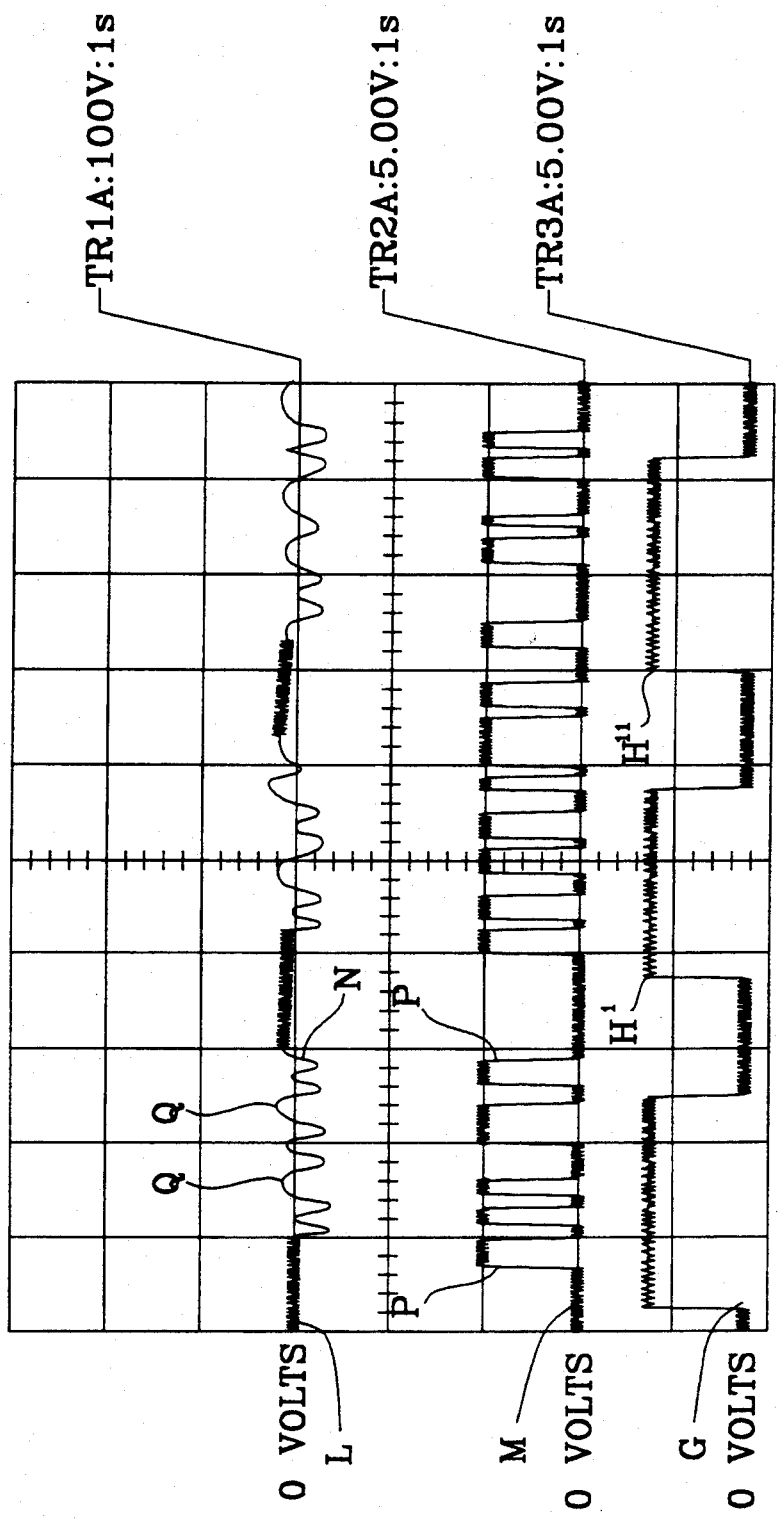
FIG. 25 is a trace of the output of the invention at points L and M in FIG. 3 when the invention is pumping water at a flow rate of 400 ml/hour and at a 50° tilt to the left relative to the central axis of the drop chamber and a trace of the pump/motor control signal.

FIGS. 20 through 22 show the signal output at points L and M for one "cycle" of the pump 17 pumping water at a flow rate of 125 ml/hour. FIGS. 23 through 26 show the signal output at points L and M for one "cycle" of the pump 17 pumping water at a flow rate of 400 ml/hour. In FIGS. 20, 23 and 24, the drop chamber 22 is vertical while in FIGS. 21, 25 and 22, 26, the drop chamber 22 is tilted 50 degrees to the left and right, respectively, of the area connecting the diodes 38 and detector 40. As can be seen, at these flow rates, one "cycle" produces considerably more than two drops at L and a corresponding number of amplified square wave signals P at M.

FIGS. 27 and 28 show the detector output signal at points L and M for one "cycle" of the pump 17 pumping Pre-Attain ®, an enteral feeding solution sold by Sherwood Medical Company, at a flow rate of 95 ml/hour. In FIG. 24, the drop chamber 22 is tilted 45 degrees to the left of the area connecting the diodes 38 and detector 40 while in FIG. 25, the drop chamber 22 is vertical. The enteral feeding fluid Pre-Attain ® is more viscous than is water. As can be seen, in each case one "cycle" produces two drops, as depicted at L, and correspondingly, two amplified square wave signals P at M.

Figure 29:
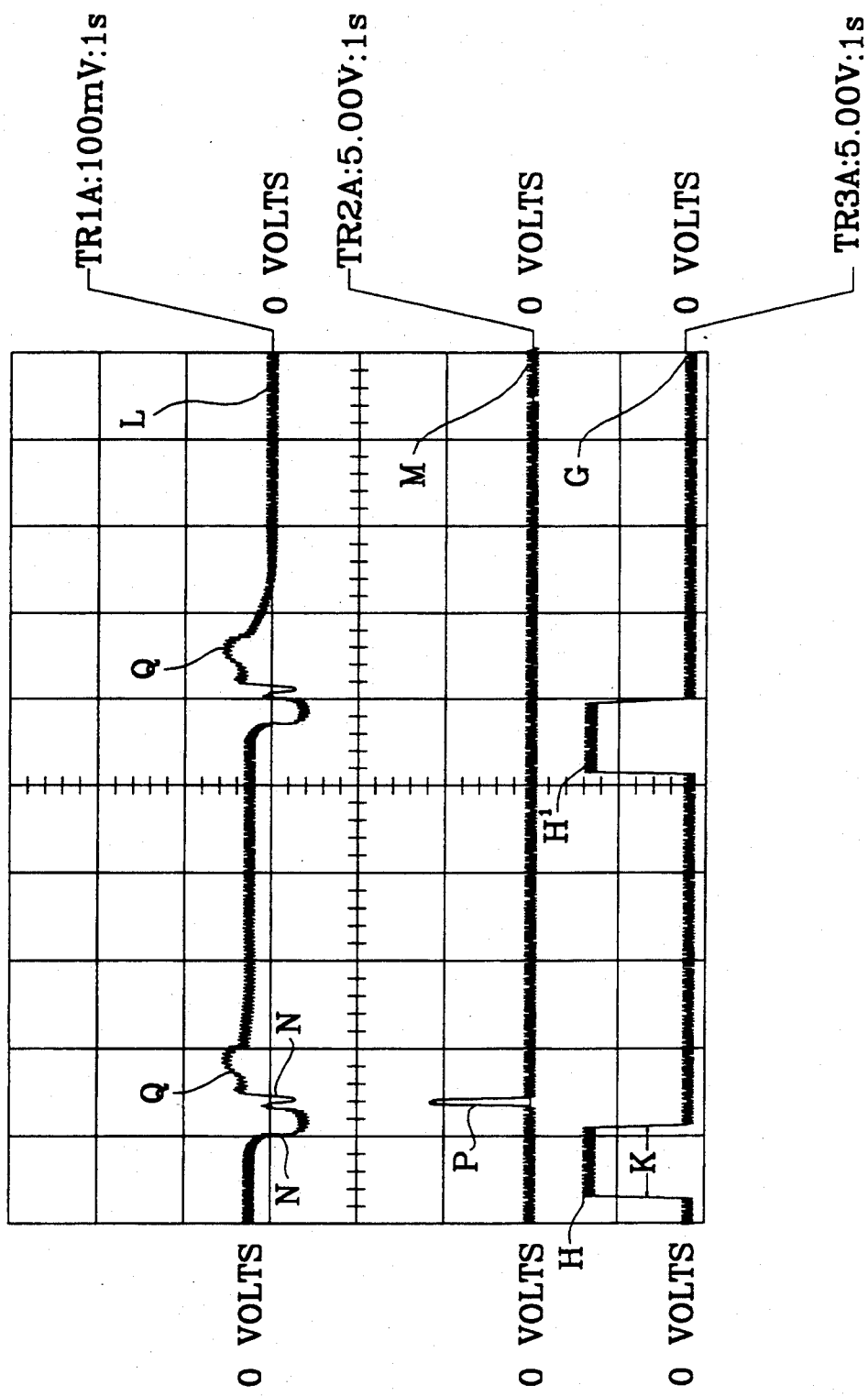
FIG. 29 is a trace of the output of the invention at points L and M in FIG. 3 when the invention is pumping water at a flow rate of 95 ml/hour and at a 0° tilt angle relative to the central axis of the drop chamber where the feeding tube is occluded and a trace of the pump motor control signal.
Figure 30:
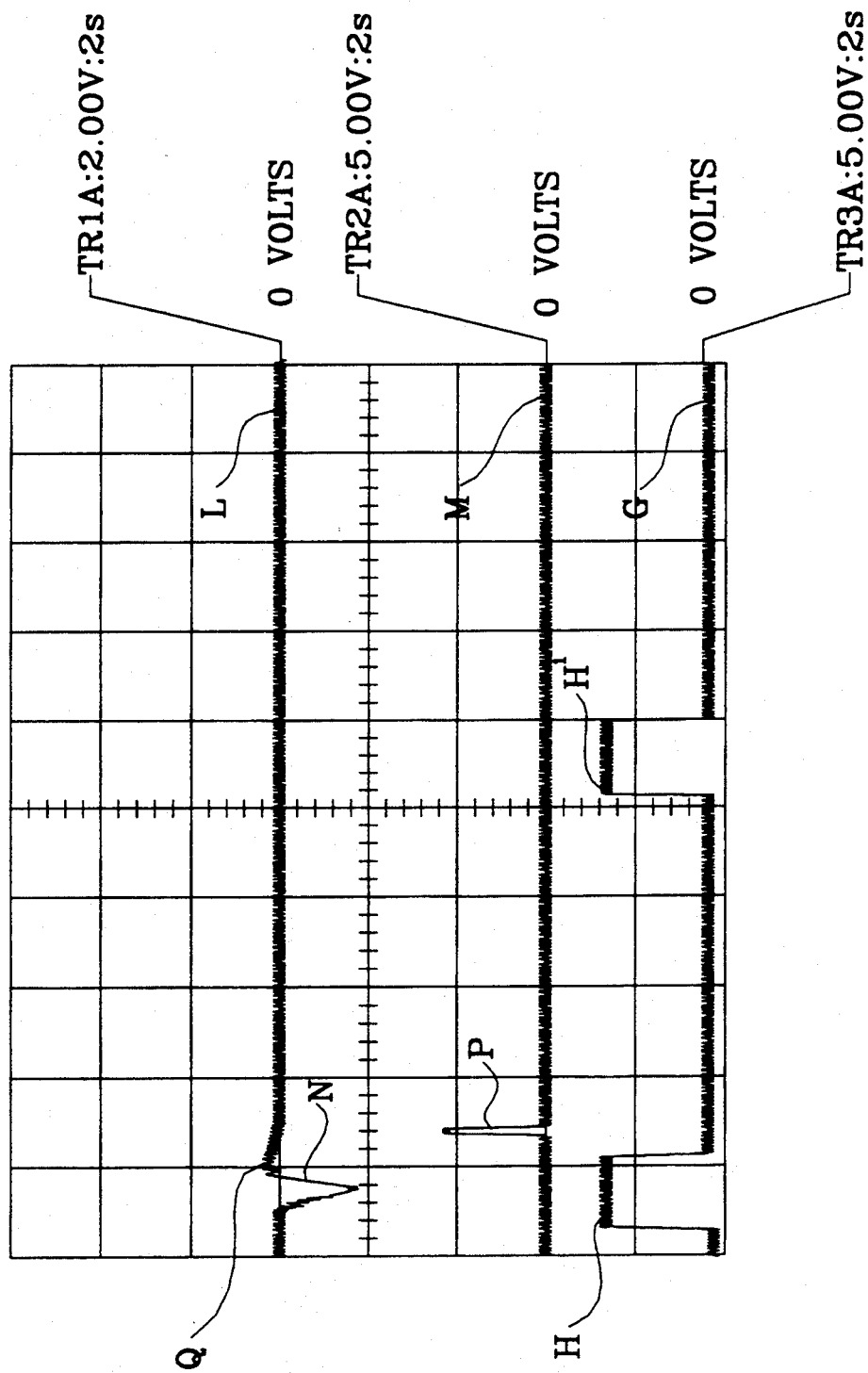
FIG. 30 is a trace of the output of the invention at points L and M in FIG. 3 when the invention is pumping water at a flow rate of 125 ml/hour and at a 0° tilt angle relative to the central axis of the drop chamber where the feeding tube is occluded and a trace of the pump motor control signal.
Figure 31:
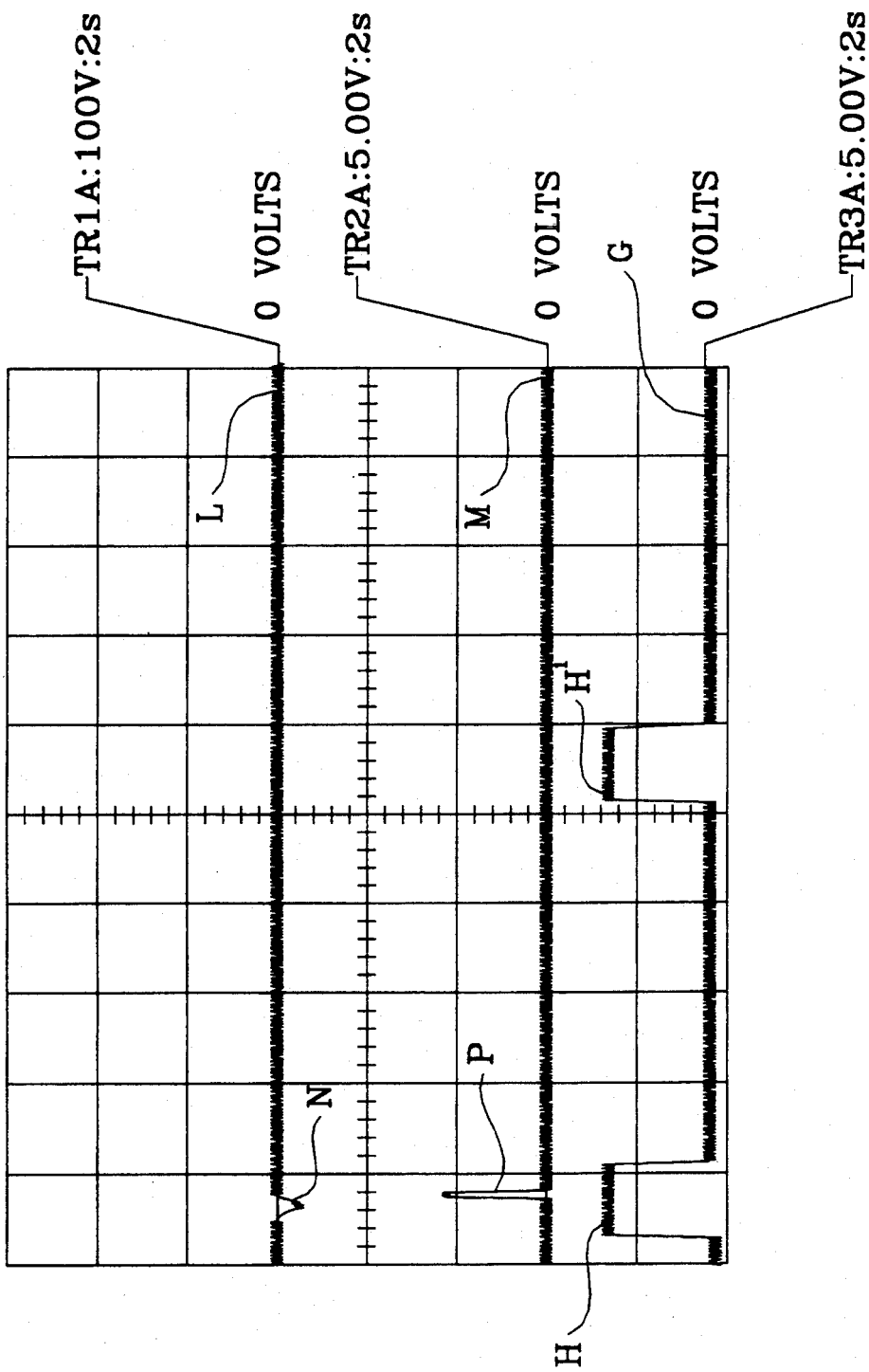
FIG. 31 is a trace of the output of the invention at points L and M in FIG. 3 when the invention is pumping water at a flow rate of 125 ml/hour and at a 50° tilt angle to the left relative to the central axis of the drop chamber where the feeding tube is occluded and a trace of the pump motor control signal.
Figure 32:
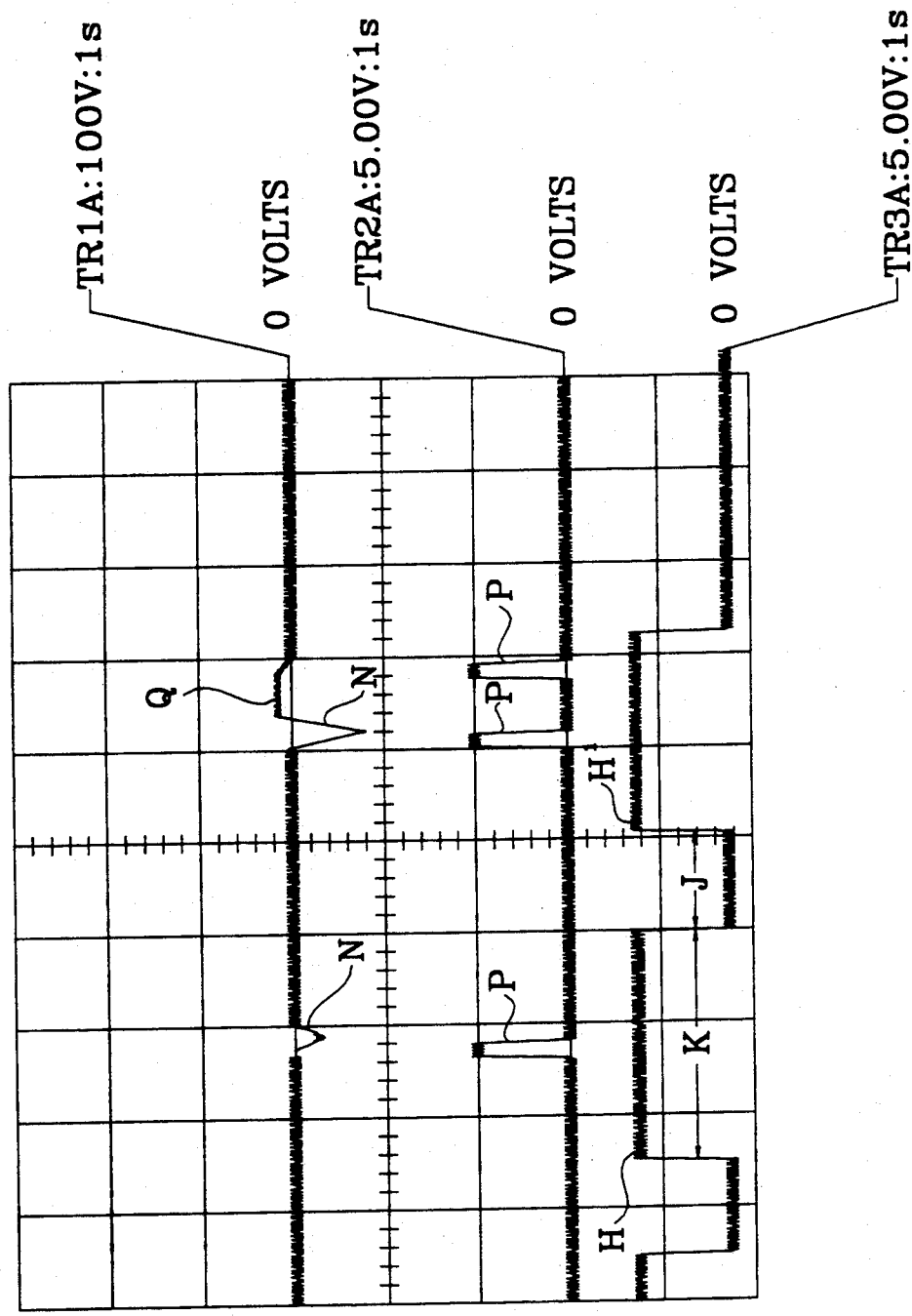
FIG. 32 is a trace of the output of the invention at points L and M in FIG. 3 when the invention is pumping water at a flow rate of 400 ml/hour and at a 0° tilt relative to the central axis of the drop chamber where the feeding tube is occluded and a trace of the pump motor control signal.

FIGS. 29 through 32 show the detector output signal at points L and M of the pump 17 pumping water at flow rates of 95 ml/hour for FIG. 29, 125 ml/hour for FIGS. 30 and 31 and 400 ml/hour for FIG. 32. In FIGS. 29, 30 and 32, the drop chamber 22 is vertical while in FIG. 31, the drop chamber 22 is tilted at an angle of 50 degrees to the left of vertical. In these Figures, the feeding tube 24 from the bottom portion 28 of the drop chamber 22 is occluded. As can be seen, only one voltage drop having a slope greater than the threshold slope is detected per "cycle". As a result only one square wave P is generated at M per "cycle".

These traces are in contradistinction to the non-occluded cases shown in FIGS. 17 through 28 where, with corresponding flow rates and orientation, a minimum of 2 and 4 drops per "cycle" as determined by the flow rate, are sensed by microprocessor 14. Consequently, in FIGS. 29 through 32, the detected drop is a pseudo-drop.

As stated, the number of drops formed and detected when the feeding tube 24 is not occluded and the pump system is operating correctly depends on the flow rate. In the preferred embodiment of the invention, at the following flow rates, the corresponding minimum number of drops per "cycle" for the number of consecutive "cycle" should be detected or a problem, most likely the occlusion of the feeding tube 24 exists:

| Flow rate in ml/hr | (Drops/"cycle")/consecutive "cycles" |
| --- | --- |
| 1–10 | 2 drops/3 "cycles" |
| 11–95 | 2 drops/4 "cycles" |
| 100–400 | 4 drops/4 "cycles" |

At the flow rate of FIGS. 29, if less than 2 drops are detected for four consecutive "cycles", microprocessor 14 determines that a problem, most likely an occlusion, exists. As a result, microprocessor 14 directs the pump 17 to stop pumping and an alarm to be generated.

Likewise, at the flow rates of FIGS. 30 through 32, if less than 4 drops are detected for four consecutive "cycles", microprocessor 14 determines that an occlusion most likely exists. Consequently, microprocessor 14 directs pump 17 to stop pumping and generates an alarm.

Figure 8:
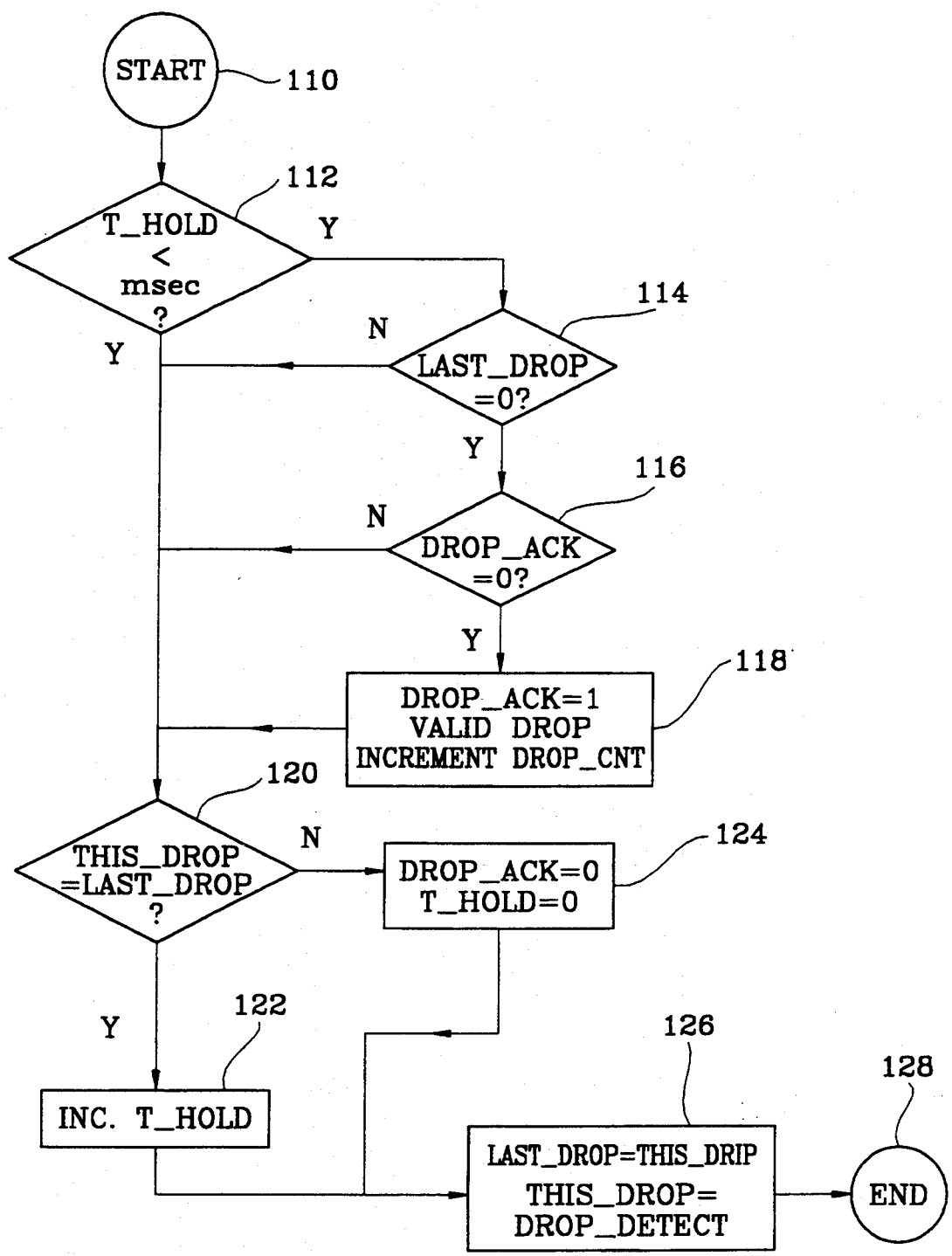
FIG. 8 is a flow chart representing the routine that determines if the drop counts are valid for the feeding profile.

FIG. 8 is a flow chart representing the process performed by microprocessor 14 to determine if a valid drop has occurred, based upon signals such as those illustrated in FIGS. 18–28. Processor 14 performs this routine every 1.87 msec. on an interrupt basis. The microprocessor 14 makes use of three software flags to keep track of the transitions in the signal received from drop detection electronics 21. The flag DROP_ACK is raised upon the occurrence of a negative transition if not previously set. The second and third flags reflect past states of DROP_DETECT, the bit in microprocessor 14 memory that shows the status of drop detection electronics 21. Flag LAST_DROP shows the status of DROP_DETECT at the end of the previous iteration; flag THIS_DROP shows that status of DROP_DETECT at the end of the current iteration.

Referring to the flow chart of FIG. 8, the present routine is entered at block 110. Timer T_HOLD is tested at block 112 to determine if 20 msec has passed since the last transition of DROP_DETECT. If 20 msec has passed, the software tests LAST_DROP in block 114 to get the status of DROP_DETECT in the previous iteration, otherwise execution passes to block 120. If LAST_DROP is low at block 114, DROP_ACK is tested in block 116, otherwise execution passes to block 120. If DROP_ACK is high at block 116, execution passes to block 120. This signifies that the drop has already been acknowledged and counted by the microprocessor 14, as will be seen below.

If DROP_ACK is low at block 116, execution passes to block 118 where flag DROP_ACK is set. This indicates that a valid drop is detected. The drop counter is also incremented in step 118.

Flags THIS_DROP and LAST_DROP are compared at block 120. If they are not equal, a transition of DROP_DETECT has occurred, and DROP_ACK and T_HOLD are reset at block 124, and execution passes to block 126; if they are equal, T_HOLD is incremented at block 122, and execution continues at block 126.

At block 126, LAST_DROP is set equal to THIS_DROP and then THIS_DROP is set equal to DROP_DETECT. The routine then ends at block 128.

It should be appreciated that, in operation, it will require many passes through the process illustrated in FIG. 8 to detect the occurrence of a valid drop. For example, upon the occurrence of a negative-going transition in the detector output signal of sufficient slope, DROP_ACK will be set to 1 at block 118.

Thereafter, blocks 112, 120, 122 and 126 are performed in repeated sequential passes until the slope of the detector output signal is no longer negative and above the threshold value, as registered by block 120. In the next pass through the routine, blocks 112, 120, 124 and 126 are performed until T_HOLD exceeds 20 msec. At this point, a valid drop is detected, and DROP_ACK is set until the next transition of DROP_DETECT, as shown in step 118.

When a waveform such as waveform 7b in FIG. 27 is encountered, it is handled in precisely the same manner as just described, except that the negative transition is detected much sooner than it was with respect to waveform 7a.

Should a signal such as waveform 7c be encountered, the initial positive and negative-going transitions are handled in the same manner as they were from waveform 7a. Whenever a transition occurs in DROP_DETECT as tested in block 120, T_MOLD and DROP_ACK are reset in block 124. This action will continue until no transitions are detected within a 20 msec window. The state of LAST DROP is then tested in block 114; if low, DROP_ACK is tested in block 116. If DROP_ACK is low, a valid drop is counted by the microprocessor 14 and DROP_ACK is set in block 118. Variable drop_cnt is incremented in order to accumulate the number of drops in a pumping "cycle".

Figure 9:
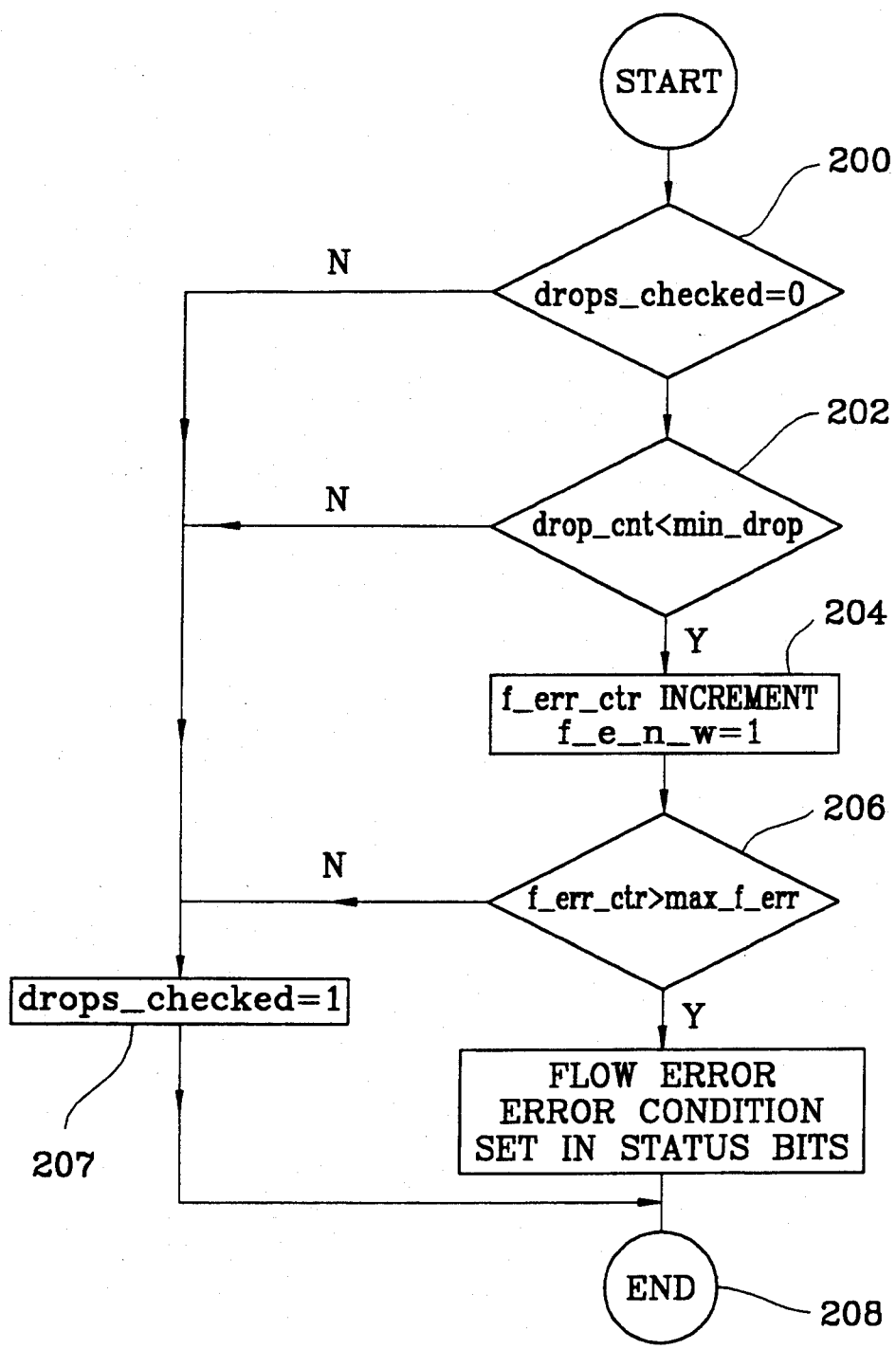
FIG. 9 is a flow chart representing the routine to variables generated elsewhere to determine whether to generate an error message.
Figure 10:
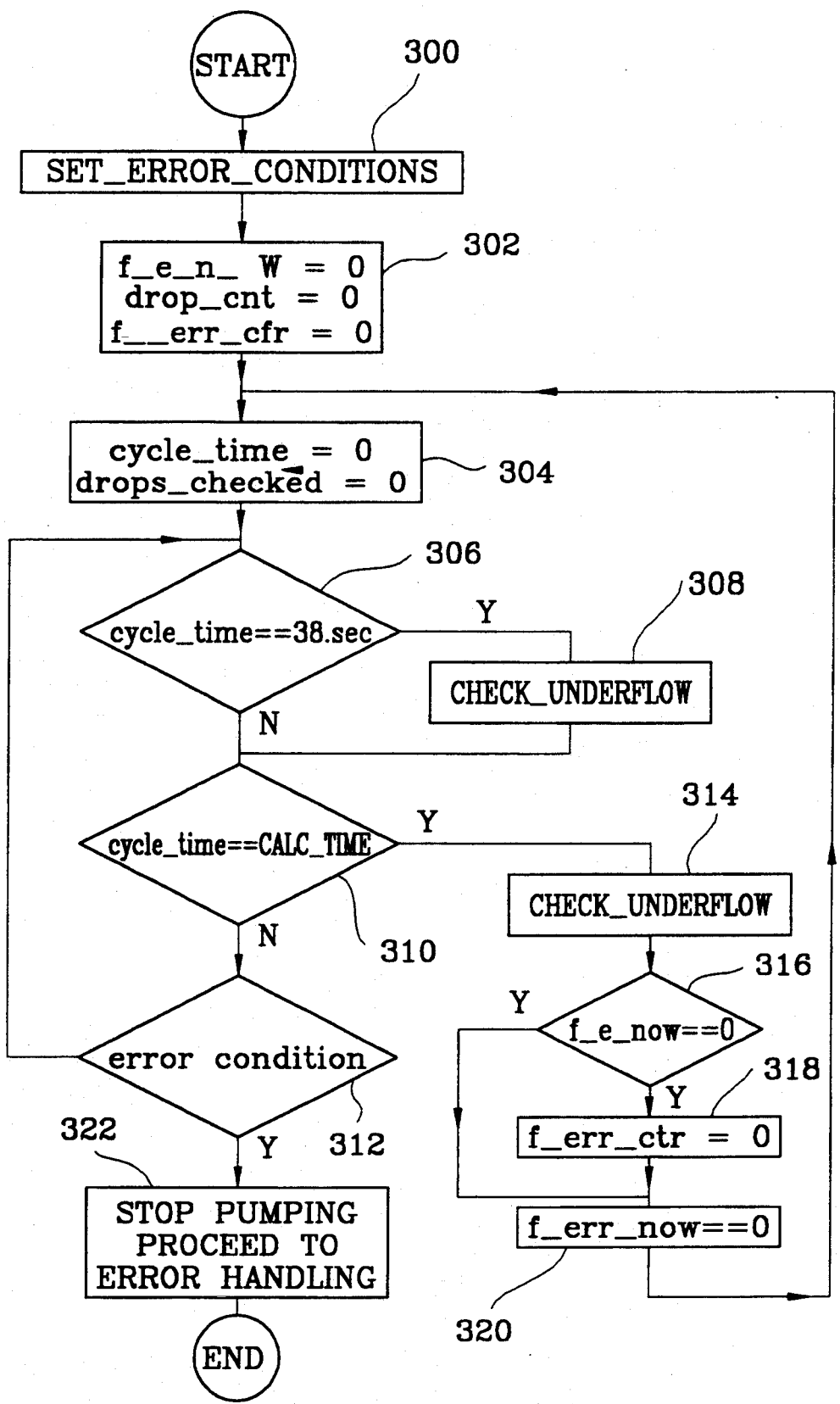
FIG. 10 is a flow chart representing the routine that implements the routines shown in FIGS. 8 and 9 during a pumping cycle.

The microprocessor has software embedded in it that allows an error message to be generated for the user. This error message warns the pump operator that an insufficient number of drops is passing through the drip chamber, due to a set occlusion or an empty formula container. FIGS. 9-11 illustrate the embodiment of software that tracks the number of drops and generates an error for the operator when certain requirements are not met.

FIG. 9 describes the setting of parameters used to determine if the drop counts are valid for the given feeding profile. After the program is started, it passes to step 100. Step 100 sets variable max_f_err equal to 4, which is the maximum number of consecutive pumping "cycles" (motor activations) that may occur with insufficient drop counts before generating an error message. From step 100, the program passes to step 102.

Step 102 tests variable flow for a value less than 100. The flow variable contains the pumping rate in units of ml/hr. If flow is greater than or equal to 100, the program passes to step 108 where variable min_drop is set to 4. From step 108, the routine terminates. The effect of this "cycle" is that the software must see 4 or more drops during a pumping "cycle" at flow rates of 100 ml/hr or greater for the "cycle" to be error-free. If flow is less than 100, control passes to step 104, where flow is again tested to see if the flow rate is lower than 6 ml/hr. If variable flow is less than 6, the program passes to step 110 where variable max_f_err is set to 3. This means that at flow rates less than 6 ml/hr, a flow error may be generated if three consecutive "cycles" have an insufficient number of drops.

If in step 104 flow is greater than or equal to 6 meaning that the flow rate is greater than or equal to 6 ml/hr, control passes to step 106. At step 106, flow is tested against the value of 11. If flow is less than 11 meaning that the flow rate is less than 11 ml/hr, the program passes to step 112 where variable max_f_err is set to 3. Otherwise, the software passes from step 106 to step 114. Step 114 sets the variable min_drop equal to 2. The routine then terminates.

In summary, FIG. 9 sets the variables max_f_err and min_drop depending on the value of flow. This is summarized below. The variable flow contains the value of the flow rate in ml/hr.

| FLOW | MAX_F_ERR | MIN_DROP |
|---|---|---|
| 1-5 | 3 | 2 |
| 6-10 | 3 | 2 |
| 11-95 | 4 | 2 |
| 100-400 | 4 | 4 |

FIG. 10 describes the testing of variables used to determine whether or not to generate an error message. This routine is only accessed when an insufficient number of drops has been detected in a pumping "cycle".

The routine starts in step 200, where bit drops_checked is tested. If this bit is set, control passes to the end of the routine, meaning that this routine has been executed at some previous time in the pumping "cycle". If bit drops_checked is not set, control then passes to step 202, where variable drop_cnt is compared to variable min_drop. Variable drop_cnt is incremented in the software described in FIG. 8. This variable accumulates the number of valid drops detected in a pumping "cycle". If drop_cnt is less than min_drop control passes to step 204. At step 204, variable f_err_ctr is incremented to accumulate the number of consecutive "cycles" with insufficient drop counts. Also at step 204, bit f_e_now is set to indicate than an insufficient drop count has occurred in the present "cycle". From step 204, the program passes to step 206. If the comparison in step 202 indicates that a sufficient number of drops has been seen for the "cycle" so that drop_cnt is greater than or equal to min_drop, the routine executes step 207 and then ends.

Step 206 compares the number of consecutive pumping "cycles" with insufficient drop counts to a threshold set previously in f_err_ctr. If variable f_err—ctr is greater than or equal to variable max_f_err, the program passes to step 208 where appropriate flags are set that later cause an error message to be displayed to the pump operator. If the comparison in step 206 is not true, the program passes to step 207 where bit drops_checked is set. After executing step 207, the routine ends.

FIG. 11 describes the use of the software in FIGS. 9 and 10 during a pumping "cycle". The routine in FIG. 11 would start when the operator commands the pump to begin delivering formula. Step 300 executes the SET_ERROR_CONDITIONS routine as described in FIG. 9 and then passes to step 302.

Step 302 resets three variables f_e_now, drop_cnt, and f_err_ctr and passes to step 304. Step 304 resets variables cycle_time (pumping "cycle" timer) and bit drops_checked. From step 304, the program passes to step 306. Step 306 tests cycle_time to see if the pumping "cycle" has gone on for approximately 38 seconds. If this is true, the program passes to step 308 where the routine check_underflow is executed as described in FIG. 10 so that the drop counts for the "cycle" are tested. From step 308, control passes to step 310. If step 306 is not true, control also passes to step 310.

Step 310 again tests cycle_time against another variable CALC_TIME. CALC_TIME is set in another piece of code, and is simply used to control the length of the pumping "cycle", and therefore the delivery rate. The pumping "cycle" is through when cycle, time equals CALC_TIME. If variable cycle_time shows that the pump is not at the end of the pumping "cycle" so that cycle_time does not equal CALC_TIME, control passes to step 312. If the pumping "cycle" is through, control passes from step 310 to step 314, where the routine check_underflow (FIG. 10) is executed. From step 314, the program proceeds to step 316, where bit f_e_now is tested. If this bit is true, an insufficient number of drops has passed through the drop chamber 22 in the current "cycle" and therefore variable f_err_ctr is not reset in step 318. Instead, the program passes from step 316 directly to step 320. Variable f_err_ctr is only reset in step 318 when a sufficient number of drops have passed through the drop chamber 22 in the current pumping "cycle" as indicated by bit f_e_now not being set in the test in step 316. From step 318, the program passes to step 320. Step 320 resets bit f_e_now before control passes back to step 304.

If an error condition is generated because of an insufficient number of drops or some other condition, the test in step 312 will break the execution of the loop described by steps 306, 310, 312, and control will pass to step 322. If no error condition is detected at step 312, the program passes to step 306. Step 322 generally stops the pumping "cycles" and allows the software to proceed to an error handler. This portion of software then ends.

From the above description of the preferred embodiments, it can be seen that the effect of movement and tilting of the drop chamber 22 on the output of the detection electronics is eliminated, while the effect of changes in ambient light are minimized. As a result, a drop chamber 22 may be accurately monitored in an ambulatory and changing environment.

While the disclosed embodiment of the invention is fully capable of achieving the results desired, it is to be understood that this embodiment has been shown and described for purposes of illustration only and not for purposes of limitation. Moreover, those skilled in the art will appreciate that many additions, modifications and substitutions are possible without departing from the scope and spirit of the invention as defined by the accompanying claims.

We claim:

1. A drop flow detector comprising:
    a drop chamber;
    a light source for passing light through said chamber;
    a light detector responsive to said light after it has passed through said chamber for producing an electrical detector output signal related thereto; and,
    circuit means, responsive to said detector output signal, for determining the existence of drop flow, including:
    means for detecting the slope of voltage changes in said detector output signal;
    means for determining that the slope detected by said means for detecting exceeds a threshold value; and,
    means, responsive to a determination by said means for determining that the slope detected by said means for detecting exceeds said threshold value, for generating a control signal.

2. The drop detector of claim 1 wherein said light detector is saturated with light emitted from said light source, thereby producing said detector output signal at a saturation level; and,
    wherein said circuit means detects the variation in said detector output signal from the saturation level when a drop passes through said drop chamber.

3. The drop detector of claim 1 wherein said circuit means for determining the existence of drop flow further includes filtering means for removing frequency components of said detector output signal above the expected frequency of drop formation, said filtering means located between said light detector and said means for detecting.

4. The drop detector of claim 3 wherein said filtering means has a variable cut-off frequency.

5. The drop detector of claim 4 wherein said detector is part of a system, said system including a motorized pump and a microprocessor for controlling the speed of said pump, said microprocessor also deriving a second control signal related to said speed, said second control signal being applied to said filtering means to vary the cut-off frequency.

6. The drop detector of claim 1 wherein said control signal has a first value when the slope of the detector output signal exceeds the threshold value and has a second value when the slope of the detector output signal does not exceed the threshold value.

7. The drop detector of claim 1 wherein said means for detecting comprises a differentiator amplifier having two inputs and an output, one of said inputs receiving said detector output signal.

8. The drop detector of claim 7 wherein said means for determining comprises means for biasing, at a constant voltage, said input of said differentiator amplifier not receiving said detector output signal, said constant voltage chosen to set the threshold value of the slope of said detector output signal to be detected.

9. The drop detector of claim 8 wherein said means for generating a control signal is said output of said differentiator amplifier.

10. The drop detector of claim 1 further comprising means for preventing ambient light from impinging on said light detector.

11. The drop detector of claim 10 wherein said means for preventing comprises an ambient light shield surrounding said drop chamber except where said light source and said light detector are directed toward said drop chamber, said shield made of material opaque to the light detected by said light detector.

12. In a drop flow detector having a drop chamber, a light source for passing light through the chamber, a light detector responsive to the light after it has passed through the chamber for producing an electrical detector output signal related thereto, the detector output signal having varying voltage levels in response to drops passing through the drop chamber between the light source and the light detector whereby the drop blocks part of the light emitted from the light source and prevents the blocked light from impinging on the light detector, circuit means responsive to the detector output signal for determining the existence of drop flow comprising:
   means for detecting the slope of voltage changes in the detector output signal;
   means for determining that the slope detected by said means for detecting exceeds a threshold value; and,
   means, responsive to a determination by said means for determining that the slope detected by said means for detecting exceeds said threshold value, for generating a control signal.

13. The drop detector of claim 12 wherein said circuit means for determining the existence of drop flow further includes filtering means for removing frequency components of said detector output signal above the expected frequency of drop formation, said filtering means located between said light detector and said means for detecting.

14. The drop detector of claim 13 wherein said filtering means has a variable cut-off frequency.

15. The drop detector of claim 14 wherein said detector is part of a system, said system including a motorized pump and a microprocessor for controlling the speed of said pump, said microprocessor also deriving a second control signal related to said speed, said second control signal being applied to said filtering means to vary the cut-off frequency.

16. The drop detector of claim 12 wherein said means for detecting comprises a differentiator amplifier having two inputs and an output, one of said inputs receiving said detector output signal.

17. The drop detector of claim 16 wherein said means for determining comprises means for biasing, at a constant voltage, said input of said differentiator amplifier not receiving said detector output signal, said constant voltage chosen to set the threshold value of the slope of said detector output signal to be detected.

18. The drop detector of claim 17 wherein said means for generating a control signal is said output of said differentiator amplifier.

19. A drop flow detector comprising:
   a drop chamber for passing a drop therethrough;
   a light source for passing light through said chamber;
   a light detector producing an electrical detector output signal responsive to said light after said light has passed through said chamber, wherein, when no drop is passing through said drop chamber between said emitter and said detector, said light emitted from said emitter saturates said detector and said resulting detector output signal is at a constant first level and, wherein, when a drop passes through said drop chamber between said emitter and said detector, a portion of the light emitted from said emitter is blocked by the drop and is prevented from impinging on said detector thereby causing said light detector to produce an electrical detector output signal at a second level which second level differs from said first level; and,
   circuit means, responsive to said detector output signal, for determining the existence of drop flow, said circuit means including means for detecting the variation in said detector output signal from said first level to said second level.

20. The drop detector of claim 19 wherein said circuit means includes:
   means for detecting the slope of voltage changes in said detector output signal;
   means for determining that the slope detected by said means for detecting exceeds a threshold value; and,
   means, responsive to a determination by said means for determining that the slope detected by said means for detecting exceeds said threshold value, for generating a control signal.

21. A drop flow detector comprising:
   a drop chamber;
   a light source for passing light through said chamber;
   a light detector responsive to said light after it has passed through said chamber for producing an electrical detector output signal related thereto, wherein said light detector is saturated with light emitted from said light source, thereby producing said detector output signal at a saturation level;
   circuit means, responsive to said detector output signal, for determining the existence of drop flow, including:
   means for detecting the slope of voltage changes in said detector output signal;
   means for determining that the slope detected by said means for detecting exceeds a threshold value; and,
   means, responsive to a determination by said means for determining that the slope detected by said means for detecting exceeds said threshold value, for generating a control signal,
   wherein said circuit means detects the variation in said detector output signal from the saturation level when a drop passes through said drop chamber.

22. A drop flow detector comprising:
   a drop chamber;
   a light source for passing light through said chamber;
   a light detector responsive to said light after it has passed through said chamber for producing an electrical detector output signal related thereto, wherein said light detector is saturated with light emitted from said light source thereby producing said detector output signal at a saturation level;
   circuit means, responsive to said detector output signal, for determining the existence of drop flow, including:

means for detecting the slope of voltage changes in said detector output signal, said means for detecting comprising a differentiator amplifier having two inputs and an output, one of said inputs receiving said detector output signal;

means for determining that the slope detected by said means for detecting exceeds a threshold value, said means for determining comprising means for biasing, at a constant voltage, said input of said differentiator amplifier not receiving said detector output signal, said constant voltage chosen to set said threshold value of the slope of said detector output signal to be detected;

means, responsive to a determination by said means for determining that the slope detected by said means for detecting exceeds said threshold value, for generating a control signal, said means for generating a control signal being said output of said differentiator amplifier, said control signal having a first value when the slope of the detector output signal exceeds said threshold value and having a second value when the slope of the detector output signal does not exceed said threshold value;

wherein said circuit means detects the variation in said detector output signal from the saturation level when a drop passes through said drop chamber; and, filtering means for removing frequency components of said detector output signal above the expected frequency of drop formation, said filtering means located between said light detector and said means for detecting, said filtering means having a variable cut-off frequency;

wherein said detector is part of a system, said system including a motorized pump and a microprocessor for controlling the speed of said pump, said microprocessor also deriving a second control signal related to said speed, said second control signal being applied to said filtering means to vary the cut-off frequency.

23. A method for detecting drops passing through a drop chamber having a light source passing light through the chamber and a light detector responsive to the light after it has passed through the chamber, the light detector producing an electrical detector output signal related to the amount of light impinging on the light detector, the method comprising the steps of:

illuminating the light detector with light emitted from the light source with a sufficient intensity to saturate the light detector, thereby producing a detector output signal at a saturation level;

detecting the variation in the detector output signal from the saturation level when a drop passes through the drop chamber.

24. The method of claim 23 further comprising the step of shielding the drop chamber with a shield made of material opaque to the light detected by the light detector, said shield surrounding the drop chamber except where the light source and the light detector are directed toward the drop chamber.

25. A method for detecting drops passing through a drop chamber having a light source passing light through the chamber and a light detector responsive to the light after it has passed through the chamber, the light detector producing an electrical detector output signal related thereto, the method comprising the steps of:

detecting the slope of voltage changes in the detector output signal;

determining that the slope detected exceeds a threshold value; and, generating, is response to a determination that the slope detected exceeds said threshold value, a control signal.

* * * * *